US010385350B2

(12) United States Patent
Acton et al.

(10) Patent No.: US 10,385,350 B2
(45) Date of Patent: Aug. 20, 2019

(54) TRANSCRIPT OPTIMIZED EXPRESSION ENHANCEMENT FOR HIGH-LEVEL PRODUCTION OF PROTEINS AND PROTEIN DOMAINS

(71) Applicant: Rutgers, The State University of New Jersey, New Brunswick, NJ (US)

(72) Inventors: Thomas B. Acton, New Brunswick, NJ (US); Stephen Anderson, New Brunswick, NJ (US); Yuanpeng Janet Huang, New Brunswick, NJ (US); Gaetano Montelione, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 54 days.

(21) Appl. No.: 14/883,277

(22) Filed: Oct. 14, 2015

(65) Prior Publication Data
US 2016/0201068 A1    Jul. 14, 2016

Related U.S. Application Data

(63) Continuation of application No. 14/357,484, filed as application No. PCT/US2012/064836 on Nov. 13, 2012, now abandoned.

(60) Provisional application No. 61/558,277, filed on Nov. 10, 2011.

(51) Int. Cl.
*C12N 15/70* (2006.01)
*C12N 15/74* (2006.01)
*C12N 15/67* (2006.01)
*C12P 21/00* (2006.01)

(52) U.S. Cl.
CPC ............ *C12N 15/70* (2013.01); *C12N 15/67* (2013.01); *C12P 21/00* (2013.01)

(58) Field of Classification Search
None
See application file for complete search history.

(56) References Cited

U.S. PATENT DOCUMENTS

2014/0273091 A1    9/2014    Acton

FOREIGN PATENT DOCUMENTS

WO    1989000604 A1    1/1989
WO    2006097945 A2    9/2006

OTHER PUBLICATIONS

Acton, et al., "Preparation of Protein Samples for NMR Structure, Function, and Small-Molecule Screening Studies", Methods in Enzymology 493, 21-60 (2011).
Agaton, et al., "Affinity Proteomics for Systematic Protein Profiling of Chromosome 21 Gene Products in Human Tissues", Molecular & Cellular Proteomics 2, 405-414 (2003).
Altschul, et al., "Basic local alignment search tool", J Mol Biol 215, 403-410 (1990).
Anderson, "Production of Human Transcription Factor Immunogens", NIH Protein Capture Reagents Meeting, Bethesda, Maryland, 26 pages, Dec. 15-16, 2011.
Better, et al., "Expression of Engineered Antibodies and Antibody Fragments in Microorganisms", Methods in Enzymology 178, 476-496 (1989).
Bindewald, et al., "CyloFold: secondary structure prediction including pseudoknots", Nucleic Acids Res 38, W368-372 (2010).
Bird, et al., "Single Chain Antibody Variable Regions", Tibtech 9, 132-137 (1991).
Brodskii, et al., "GeneBee-NET: An Internet based server for biopolymer structure analysis", Biokhimiia 60(8), 1221-1230 (1995). [English Abstract Only].
Co, et al., "A humanized antibody specific for the platelet integrin gpIIb/IIIa", J Immunol 152, 2968-2976 (1994).
Corpet, "Multiple sequence alignment with hierarchical clustering", Nucl Acids Res 16, 10881-10890 (1988).
Crowe, et al., "6xHis-Ni-NTA chromatography as a superior technique in recombinant protein expression/purification", Methods Mol Biol 31, 371-387 (1994).
Ding, et al., "Sfold web server for statistical folding and rational design of nucleic acids", Nucleic Acids Res 32, W135-141 (2004).
Do, et al., "CONTRAfold: RNA secondary structure prediction without physics-based models", Bioinformatics 22, e90-e98 (2006).
Gonzalez De Valdivia, et al., "A codon window in mRNA downstream of the initiation codon where NGG codons give strongly reduced gene expression in *Escherichia coli*", Nucleic Acids Res 32, 5198-5205 (2004).
Gruber, et al., "The Vienna RNA websuite", Nucleic Acids Res 36, W70-74 (2008).
Hamada, et al., "Predictions of RNA secondary structure by combining homologous sequence information", Bioinformatics 25, i330-8 (2009).
Higgins, et al., "Fast and sensitive multiple sequence alignments on a microcomputer", Comput Appl Biosci 5(2), 151-153 (1989).
Huang, et al., "Directed evolution of the 5'-untranslated region of the phoA gene in *Escherichia coli* simultaneously yields a stronger promoter and a stronger Shine-Dalgarno sequence", Biotechnol J, vol. 1, 1275-1282 (2006).
Huang, et al., "Parallelization of a local similarity algorithm", CABIOS 8, 155-165 (1992).
Huston, et al., "Protein engineering of antibody binding sites: Recovery of specific activity in an anti-digoxin single-chain Fv analogue produced in *Escherichia coli*", Proc. Natl. Acad. Sci. 85, 5879-5883 (1988).
Jansson, et al., "High-level production of uniformly [15]N- and $^{13}$C-enriched fusion proteins in *Escherichia coli*", J Biomol NMR 7, 131-141 (1996).
Jia, et al., "The relationship among gene expression, folding free energy and codon usage bias in *Escherichia coli*", FEBS Letters 579, 5333-5337 (2005).

(Continued)

*Primary Examiner* — Channing S Mahatan
(74) *Attorney, Agent, or Firm* — Viksnins Harris Padys Malen LLP

(57) ABSTRACT

The present invention relates to a system for high-level production of recombinant proteins and protein domains.

22 Claims, 17 Drawing Sheets
Specification includes a Sequence Listing.

(56) References Cited

OTHER PUBLICATIONS

Kapust, et al., "The P1' specificity of tobacco etch virus protease", Biochem Biophys Res Commun 294, 949-955 (2002).

Karlin, et al., "Applications and statistics for multiple high-scoring segments in molecular sequences", Proc Natl Acad Sci 90, 5873-5877 (1993).

Karlin, et al., "Methods for assessing the statistical significance of molecular sequence features by using general scoring schemes", Proc Natl Acad Sci 87(6), 2264-2268 (1990).

Kudla, et al., "Coding-sequence determinants of gene expression in *Escherichia coli*", Science 324, 255-258 (2009).

Lamla, et al., "The Nano-tag, a streptavidin-binding peptide for the purification and detection of recombinant proteins", Protein Expr Purif 33, 39-47 (2004).

Lamoyi, "Preparation of F(ab')2 fragments from mouse IgG of various subclasses", Methods Enzymol 121, 652-663 (1986).

Liu, et al., "Loopy proteins appear conserved in evolution", J Mol Biol 322, 53-64 (2002).

Markham, et al., "UNAFold: software for nucleic acid folding and hybridization", Methods Mol Biol 453, 3-31 (2008).

Mathews, et al., "Incorporating chemical modification constraints into a dynamic programming algorithm for prediction of RNA secondary structure", Proc Natl Acad Sci 101, 7287-7292 (2004).

Milstein, et al., "Preparation of Monoclonal Antibodies: Strategies and Procedures", Methods Enzymol. 73, 3-46 (1981).

Myers, et al., "Optimal alignments in linear space", CABIOS 4 (1), 11-7 (1988).

Netzer, et al., "Recombination of protein domains facilitated by co-translational folding in eukaryotes", Nature 358 (6640), 343-349 (1997).

Nomura, et al., "Influence of messenger RNA secondary structure on translation efficiency", Nucleic Acids Symp Ser 173-176 (1984).

Paik, et al., "The Influence of the Nucleotide Sequences of Random Shine-Dalgarno and Spacer Region on Bovine Growth Hormone Gene Expression", Journal of Microbiology 44 (1), 64-71 (2006).

Patent Cooperation Treaty, International Searching Authority, Search Report and Written Opinion for PCT/US2012/064836, 11 pages, dated May 29, 2013.

Pearson, et al., "Improved tools for biological sequence comparison", Proc Natl Acad Sci 85, 2444-2448 (1988).

Pearson, "Using the FASTA program to search protein and DNA sequence databases", Metho Mol Biol 24, 307-331 (1994).

Pluckthun, et al., "Expression of functional antibody Fv and Fab fragments in *Escherichia coli*", Methods Enzymol 178, 497-515 (1989).

Quan, et al., "Parallel on-chip gene synthesis and application to optimization of protein expression", Nat Biotechnol 29, 449-452 (2011).

Reeder, et al., "pknotsRG: RNA pseudoknot folding including near-optimal structures and sliding windows", Nucleic Acids Res 35, W320-324 (2007).

Rivas, et al., "A dynamic programming algorithm for RNA structure prediction including pseudoknots", J Mol Biol 285, 2053-2068 (1999).

Rocha, et al., "Translation in Bacillus subtilis: roles and trends of initiation and termination, insights from a genome analysis", Nucleic Acids Res 27, 3567-3576 (1999).

Rousseaux, et al., "Optimal conditions for the preparation of proteolytic fragments from monoclonal IgG of different rat IgG subclasses", Methods Enzymol 121, 663-669 (1986).

Scholle, et al., "In vivo biotinylated proteins as targets for phage-display selection experiments", Protein Expr Purif 37, 243-252 (2004).

Schroeder, et al., "Ensemble of secondary structures for encapsidated satellite tobacco mosaic virus RNA consistent with chemical probing and crystallography constraints", Biophys J 101, 167-175 (2011).

Sharp, et al., "The codon Adaptation Index—a measure of directional synonymous codon usage bias, and its potential applications", Nucleic Acids Res 15 (3), 1281-1295 (1987).

Smith, et al., "Comparison of biosequences", Advances in Applied Mathematics, vol. 2(4), 482-489 (1981).

Voss, et al., "Complete probabilistic analysis of RNA shapes", BMC Biol 4, 5 (2006).

Xayaphoummine, et al., "Kinefold web server for RNA/DNA folding path and structure prediction including pseudoknots and knots", Nucleic Acids Res 33, W605-610 (2005).

Xayaphoummine, et al., "Prediction and statistics of pseudoknots in RNA structures using exactly clustered stochastic simulations", Proc Natl Acad Sci 100, 15310-15315 (2003).

Zuker, et al., "Optimal computer folding of large RNA sequences using thermodynamics and auxiliary information", Nucleic Acids Res 9, 133-148 (1981).

FIGURE 8

|   | Target | pET15 NESG | | | pNESG Avi6HT | | | pNESG Nano6HT | | |
|---|---|---|---|---|---|---|---|---|---|---|
|   |   | E | S | ES | E | S | ES | E | S | ES |
| 1 | HR3023-1-506 | 4 | 4 | 16 | 5 | 1 | 5 | 4 | 5 | 20 |
| 2 | HR4485B-103-188 | 3 | 2 | 6 | 4 | 1 | 4 | 3 | 4 | 12 |
| 3 | HR4538D | 0 | 0 | 0 | 5 | 5 | 25 | 4 | 3 | 12 |
| 4 | HR4622-24-281 | 5 | 5 | 25 | 5 | 5 | 25 | 4 | 5 | 20 |
| 5 | HR4635D-55-161 | 3 | 4 | 12 | 5 | 2 | 10 | 4 | 0 | 0 |
| 6 | HR4670B-55-202 | 4 | 4 | 16 | 5 | 5 | 25 | 3 | 5 | 15 |
| 7 | HR4753B-182-262 | 3 | 3 | 9 | 2 | 2 | 4 | 0 | 0 | 0 |
| 8 | HR5518A-127-207 | 4 | 4 | 16 | 3 | 5 | 15 | 4 | 5 | 20 |
| 9 | HR6383B-119-195 | 4 | 4 | 16 | 4 | 2 | 8 | 3 | 1 | 3 |
| 10 | HR6489A | 2 | 0 | 0 | 5 | 3 | 15 | 4 | 4 | 16 |
| 11 | HR6490A | 0 | 0 | 0 | 4 | 4 | 16 | 3 | 3 | 9 |
| 12 | HR6490A-30-371 | 0 | 0 | 0 | 5 | 4 | 20 | 3 | 3 | 9 |
| 13 | HR6832 | 0 | 0 | 0 | 5 | 0 | 0 |   |   |   |
| 14 | HR6832-1-194 | 3 | 0 | 0 | 5 | 0 | 0 |   |   |   |
| 15 | HR6832A-33-194 | 3 | 0 | 0 | 5 | 0 | 0 |   |   |   |
| 16 | HR6832A-72-207 | 5 | 0 | 0 | 5 | 0 | 0 |   |   |   |
| 17 | HR6956-16-584 | 0 | 0 | 0 | 0 | 0 | 0 | 0 | 0 | 0 |
| 18 | HR6956A-115-584 | 0 | 0 | 0 |   |   |   | 0 | 0 | 0 |
| 19 | HR6956B-170-584 | 5 | 0 | 0 | 4 | 4 | 16 | 0 | 0 | 0 |
| 20 | HR6956B-181-584 | 3 | 0 | 0 | 4 | 0 | 0 | 0 | 0 | 0 |
| 21 | HR6956B-218-584 | 0 | 0 | 0 | 5 | 5 | 25 | 0 | 0 | 0 |
| 22 | HR6956C-115-183 | 4 | 5 | 20 | 5 | 1 | 5 | 5 | 2 | 10 |
| 23 | HR6956C-115-200 | 0 | 0 | 0 | 4 | 0 | 0 | 3 | 3 | 9 |
| 24 | HR7049A-49-474 | 0 | 0 | 0 | 3 | 0 | 0 | 3 | 0 | 0 |
| 25 | HR7049B-117-474 | 0 | 0 | 0 | 5 | 0 | 0 | 5 | 0 | 0 |
| 26 | HR7049C-49-143 | 2 | 5 | 10 | 5 | 5 | 25 | 4 | 3 | 12 |
| 27 | HR7049C-49-159 | 4 | 5 | 20 | 4 | 5 | 20 | 5 | 3 | 15 |
| 28 | HR7049C-58-159 | 0 | 0 | 0 | 5 | 3 | 15 | 4 | 3 | 12 |
| 29 | HR7097A-77-146 | 0 | 0 | 0 | 0 | 0 | 0 | 5 | 1 | 5 |
| 30 | HR7097A-77-168 | 0 | 0 | 0 | 5 | 3 | 15 | 5 | 2 | 10 |
| 31 | HR7097B-179-423 | 4 | 4 | 16 | 4 | 2 | 8 | 5 | 3 | 15 |
| 32 | HR7097C-193-423 | 4 | 0 | 0 | 5 | 2 | 10 | 5 | 0 | 0 |
| 33 | HR7130A-202-461 | 4 | 0 | 0 | 5 | 2 | 10 | 4 | 1 | 4 |
| 34 | HR7130B-104-206 | 0 | 0 | 0 | 5 | 3 | 15 | 5 | 3 | 15 |
| 35 | HR7133A-97-168 | 0 | 0 | 0 | 4 | 3 | 12 | 2 | 0 | 0 |
| 36 | HR7133A-97-174 | 0 | 0 | 0 | 2 | 5 | 10 | 0 | 0 | 0 |
| 37 | HR7133A-97-187 | 3 | 0 | 0 | 2 | 5 | 10 | 2 | 0 | 0 |
| 38 | HR7133B-182-468 | 5 | 0 | 0 | 5 | 0 | 0 | 5 | 0 | 0 |
| 39 | HR7133C-192-468 | 5 | 0 | 0 | 5 | 0 | 0 | 5 | 0 | 0 |

FIGURE 8 (CONT.)

| # | Name | | | | | | | | | |
|---|---|---|---|---|---|---|---|---|---|---|
| 40 | HR7224B-363-626 | 0 | 0 | 0 | 3 | 0 | 0 | 0 | 0 | 0 |
| 41 | HR7224B-396-626 | 0 | 0 | 0 | 1 | 0 | 0 | 0 | 0 | 0 |
| 42 | HR7224B-411-626 | 0 | 0 | 0 | 5 | 0 | 0 | 0 | 0 | 0 |
| 43 | HR7224C-291-374 | 0 | 0 | 0 | 5 | 5 | 25 | 5 | 5 | 25 |
| 44 | HR7224C-294-356 | 0 | 0 | 0 | 2 | 0 | 0 | 5 | 0 | 0 |
| 45 | HR7370A-209-460 | 0 | 0 | 0 | 5 | 0 | 0 | 5 | 0 | 0 |
| 46 | HR7372A-210-470 | 5 | 0 | 0 | 5 | 0 | 0 | 5 | 0 | 0 |
| 47 | HR7372A-237-470 | 3 | 0 | 0 | 5 | 0 | 0 | 0 | 0 | 0 |
| 48 | HR7372A-245-470 | 3 | 0 | 0 | 5 | 0 | 0 | 3 | 0 | 0 |
| 49 | HR7378A-18-385 | 0 | 0 | 0 | 0 | 0 | 0 | 5 | 0 | 0 |
| 50 | HR7378B-65-385 | 4 | 0 | 0 | 5 | 0 | 0 | 2 | 0 | 0 |
| 51 | HR7378B-76-385 | 0 | 0 | 0 | 5 | 0 | 0 | 2 | 0 | 0 |
| 52 | HR7378C-18-109 | 0 | 0 | 0 | 4 | 2 | 8 | 5 | 0 | 0 |
| 53 | HR7378C-18-83 | 0 | 0 | 0 | 4 | 2 | 8 | 4 | 0 | 0 |
| 54 | HR7378C-18-96 | 0 | 0 | 0 | 5 | 2 | 10 | 5 | 2 | 10 |
| 55 | HR7469A-9-91 | 0 | 0 | 0 | 3 | 0 | 0 | 0 | 0 | 0 |
| 56 | HR7469A-9-95 | 0 | 0 | 0 | 0 | 0 | 0 | 0 | 0 | 0 |
| 57 | HR7469B-103-328 | 5 | 0 | 0 | 5 | 0 | 0 | 5 | 0 | 0 |
| 58 | HR7475A-6-105 | 0 | 0 | 0 | 5 | 3 | 15 | 5 | 4 | 20 |
| 59 | HR7475A-6-120 | 0 | 0 | 0 | 4 | 2 | 8 | 5 | 2 | 10 |
| 60 | HR7475B-6-77 | 4 | 4 | 16 | 3 | 1 | 3 | 5 | 2 | 10 |
| 61 | HR7475B-6-82 | 5 | 5 | 25 | 3 | 0 | 0 | 5 | 3 | 15 |
| 62 | HR7475C-103-352 | 5 | 0 | 0 | 5 | 2 | 10 | 4 | 0 | 0 |
| 63 | HR7515A-85-154 | 4 | 4 | 16 | 3 | 5 | 15 | 5 | 2 | 10 |
| 64 | HR7515A-85-166 | 3 | 4 | 12 | 3 | 4 | 12 | 3 | 5 | 15 |
| 65 | HR7515A-97-166 | 3 | 5 | 15 | 2 | 0 | 0 | 4 | 2 | 8 |
| 66 | HR7515B-178-423 | 4 | 0 | 0 | 4 | 1 | 4 | 4 | 0 | 0 |
| 67 | HR7515C-183-417 | 4 | 0 | 0 | 5 | 1 | 5 | 5 | 0 | 0 |
| 68 | HR7515D-84-169 | 4 | 3 | 12 | 4 | 5 | 20 | 3 | 3 | 9 |
| 69 | HR7522A-142-391 | 0 | 0 | 0 | 5 | 2 | 10 | 5 | 0 | 0 |
| 70 | HR7522B-142-378 | 4 | 0 | 0 | 5 | 2 | 10 | 4 | 0 | 0 |
| 71 | HR7522C-148-377 | 4 | 0 | 0 | 5 | 2 | 10 | 5 | 0 | 0 |
| 72 | HR7522D-58-135 | 0 | 0 | 0 | 4 | 2 | 8 | 3 | 3 | 9 |
| 73 | HR7564B-16-125 | 0 | 0 | 0 | 5 | 3 | 15 | 5 | 2 | 10 |
| 74 | HR7636B-113-394 | 0 | 0 | 0 | 5 | 1 | 5 | 5 | 0 | 0 |
| 75 | HR7785A-601-673 | 0 | 0 | 0 | 5 | 2 | 10 | 3 | 1 | 3 |
| 76 | HR7785A-601-685 | 0 | 0 | 0 | 3 | 3 | 9 | 4 | 1 | 4 |
| 77 | HR7785B-712-984 | 0 | 0 | 0 | 5 | 0 | 0 | 3 | 0 | 0 |
| 78 | HR7870A-37-107 | 0 | 0 | 0 | 5 | 3 | 15 | 4 | 2 | 8 |
| 79 | HR7870A-37-130 | 0 | 0 | 0 | 3 | 5 | 15 | 4 | 3 | 12 |
| 80 | HR7870B-130-434 | 5 | 0 | 0 | 5 | 1 | 5 | 5 | 0 | 0 |
| 81 | HR7870C-142-434 | 5 | 0 | 0 | 5 | 0 | 0 | 5 | 0 | 0 |
| 82 | HR7906B-114-410 | 5 | 5 | 25 | 5 | 0 | 0 | 5 | 2 | 10 |
| 83 | HR7906C-50-126 | 0 | 0 | 0 | 3 | 1 | 3 | 5 | 0 | 0 |

FIGURE 8 (CONT.)

| | | | | | | | | | | |
|---|---|---|---|---|---|---|---|---|---|---|
| 84 | HR7993A-220-461 | 5 | 0 | 0 | 5 | 1 | 5 | 5 | 0 | 0 |
| 85 | HR7993B-10-111 | 4 | 3 | 12 | 5 | 5 | 25 | 4 | 3 | 12 |
| 86 | HR8028A-67-146 | 0 | 0 | 0 | 5 | 0 | 0 | 1 | 0 | 0 |
| 87 | HR8028A-67-156 | 0 | 0 | 0 | 4 | 0 | 0 | 1 | 0 | 0 |
| 88 | HR8028A-73-146 | 0 | 0 | 0 | 4 | 3 | 12 | 1 | 2 | 2 |
| 89 | HR8028A-73-156 | 0 | 0 | 0 | 3 | 1 | 3 | 4 | 0 | 0 |
| 90 | HR8028B-163-441 | 4 | 0 | 0 | 5 | 0 | 0 | 4 | 0 | 0 |
| 91 | HR8234A-206-287 | 2 | 2 | 4 | 5 | 1 | 5 | | | |
| 92 | HR8241A-261-342 | 0 | 0 | 0 | 5 | 5 | 25 | 3 | 5 | 15 |
| 93 | HR8241A-264-328 | 0 | 0 | 0 | 2 | 0 | 0 | 4 | 0 | 0 |
| 94 | HR8241B-328-598 | 0 | 0 | 0 | 5 | 0 | 0 | 0 | 0 | 0 |
| 95 | HR8278A-123-216 | 0 | 0 | 0 | 4 | 4 | 16 | 3 | 0 | 0 |
| 96 | HR8341A-100-171 | 0 | 0 | 0 | 3 | 1 | 3 | 3 | 2 | 6 |
| 97 | HR8341A-100-181 | 0 | 0 | 0 | 5 | 2 | 10 | 2 | 5 | 10 |
| 98 | HR8341A-100-200 | 0 | 0 | 0 | 4 | 2 | 8 | 4 | 1 | 4 |
| 99 | HR8341B-381-579 | 5 | 4 | 20 | 5 | 3 | 15 | 5 | 2 | 10 |

FIGURE 9

| Construct id | HUGO id | UniProt id | First 15 AA | Last 15 AA | Construct length | First 15 AA (SEQ ID NO) | Last 15 AA (SEQ ID NO) |
|---|---|---|---|---|---|---|---|
| HR6941B-732-822-Av6HT | ANAPC2 | Q9UJX6 | SDDESDSGMASQADQ | LVYSAGVYRLPKNCS | 91 | 20 | 184 |
| HR8423A-486-593-Av6HT | ANKZF1 | Q9H8Y5 | AKAPGQPELWNALLA | STRNEFRRFMEKNPD | 108 | 21 | 185 |
| HR7542A-507-616-NHT | ARID2 | Q68CP9 | QHVAPPGIVEIDSE | RAIPLPIQMYYQQQP | 110 | 22 | 186 |
| HR4394C-15 | ARID3A | Q99856 | PDHGDWTYEEQFKQL | ELQAAIDSNRREGRR | 134 | 23 | 187 |
| HR8413A-12-132-Av6HT | BACH2 | Q9BYV9 | MYVYESTVHCTNILL | MHNLEDSCFSFLQTQ | 122 | 24 | 188 |
| HR6459A-34-118-14 | BATF | Q16520 | EKNRIAAQKSRQRQT | PEVVYSAHAFHQPHV | 85 | 25 | 189 |
| HR6995B-633-746-TEV | BRPF1 | P55201 | FLILLRKTLEQLQEK | GAVLRQARRQAEKMG | 108 | 26 | 190 |
| HR8142A-104-176-Av6HT | BSX | Q3C1V8 | PGKHCRRRKARTVFS | RMKHKKQLRKSQDEP | 73 | 27 | 191 |
| HR8150A-1916-1982-Av6HT | CASP8AP2 | Q9UKL3 | NVIKKKGEIIILWTR | RFQQLMKLFEKSKCR | 66 | 28 | 192 |
| HR7269A-2-135-TEV | CBFB | Q13951 | MPRVVPDQRSKFENE | GMGCLEFDEERAQQE | 135 | 29 | 193 |
| HR6520A-9-62-Av6HT | CBX2 | Q14781 | EQVFAAECILSKRLR | NILDPRLLLAFQKKE | 54 | 30 | 194 |
| HR7064A-185-251-Av6HT | CDX2 | Q99626 | TKDKYRVVYTDHQRL | RRAKERKINKKKLQQ | 67 | 31 | 195 |
| HR7557A-195-268-15 | CEBPE | Q15744 | KGKKAVNKDSLEYRL | TQELDTLRNLFRQIP | 74 | 32 | 196 |
| HR7210A-268-373-Av6HT | CHD1 | O14646 | EEEFETIERFMDCRI | TKRWLKNASPEDVEY | 106 | 33 | 197 |
| HR3016D-352-413-15 | COPS3 | Q9UNS2 | NQKDGMVSFHDNPEK | VNPQFVQKSMGSQED | 62 | 34 | 198 |
| HR7960-1-298-Av6HT | CREB3L4 | Q8TEY5 | MDLGIPDLLDAWLEP | IAQTSNKAAQTSTCV | 298 | 35 | 199 |
| HR7807A-15-94-Av6HT | CXXC1 | Q9P0U4 | EDSKSENGENAPIYC | LEIRYRHKKSRERDG | 80 | 36 | 200 |
| HR7911A-178-244-Av6HT | DBX2 | Q6ZNG2 | DSNSKARRGILRRAV | VKIWFQNRRMKWRNS | 67 | 37 | 201 |
| HR8208A-130-186-TEV | DLX3 | O60479 | RKPRTIYSSYQLAAL | QVKIWFQNRRSKFKK | 57 | 38 | 202 |
| HR8011B-255-356-15 | DMTF1 | Q9Y222 | DEINLILRIAELDVA | NSNTNSSVQHVQJRV | 102 | 39 | 203 |
| HR8202A-15-83-Av6HT | DPRX | A6NFQ7 | MHSHRKRTMFTKKQL | AKLKKAKCKHIHQKQ | 70 | 40 | 204 |
| HR7601-1-176-Av6HT | DR1 | Q01658 | MASSSGNDDDLTIPR | NQAGSSQDEEDDDDI | 176 | 41 | 205 |

FIGURE 9 (CONT.)

| Construct id | HUGO id | UniProt id | First 15 AA | Last 15 AA | Construct length | First 15 AA (SEQ ID NO) | Last 15 AA (SEQ ID NO) |
|---|---|---|---|---|---|---|---|
| HR5528A-14 | DVL2 | O14641 | TITSGSSLPDGCEGR | SEQCYVFGDLSGGC | 112 | 42 | 206 |
| HR7051B-397-504-15 | DVL3 | Q92997 | DTERLDDFHLSIHSD | CYYIFGDLCGNMANL | 108 | 43 | 207 |
| HR7307A-71-148-Av6HT | EDF1 | O60869 | DRVTLEVGKVIQQGR | GKDIGKPIEKGPRAK | 78 | 44 | 208 |
| HR7944A-1347-1411-TEV | EEA1 | Q15075 | KWAEDNEVQNCMACG | KPVRVCDACFNDLQG | 64 | 45 | 209 |
| HR7067A-200-308-15 | ELF2 | Q15723 | MNYETMGRALRYYYQ | GVARVVNITSPGHDA | 110 | 46 | 210 |
| HR7867A-45-132-TEV | ELF3 | P78545 | SNPQMSLEGTEKASW | GDQLHAQLRDLTSSS | 88 | 47 | 211 |
| HR7097C-193-423-Av6HT | ESRRA | P11474 | PVNALVSHLLVVEPE | PMHKLFLEMLEAMMD | 231 | 48 | 212 |
| HR6884A-338-443-TEV | ETV6 | P41212 | CRLLWDYVYQLLSDS | GRTDRLEHLESQELD | 106 | 49 | 213 |
| HR7150A-140-236-Av6HT | FOXD3 | Q9UJU5 | VKPPYSYIALITMAI | EDMFDNGSFLRRRKR | 97 | 50 | 214 |
| HR8000A-64-153-Av6HT | FOXJ2 | Q9P0K8 | DGKPRYSYATLITYA | YWTIDTCPDISRKRR | 90 | 51 | 215 |
| HR7608A-43-139-15 | FOXL1 | Q12952 | RAETPQKPPYSYIAL | LDPRCLDMFENGNYR | 97 | 52 | 216 |
| HR6909A-222-360-Av6HT | FOXM1 | Q08050 | PSRPSASWQNSVSER | NPELRRNMTIKTELP | 139 | 53 | 217 |
| HR5549A-14 | FOXO3 | O43524 | LPPPQPGAAGGSGQP | NKYTKSRGRAAKKKA | 140 | 54 | 218 |
| HR4783B-262-321-TEV | GATA4 | P43694 | SASRRVGLSCANCQT | PLAMRKEGIQTRKRK | 60 | 55 | 219 |
| HR8231A-242-324-Av6HT | GBX1 | Q14549 | TGAEEGAPVTAGVTA | QNRRAKWKRIKAGNV | 83 | 56 | 220 |
| HR4429D-233-315-14 | GFI1 | Q99684 | KGAGVKVESELLCTR | QHKAVHSQERSFDCK | 83 | 57 | 221 |
| HR7418A-87-176-Av6HT | GMEB2 | Q9UKD1 | EAEIVYPITCGDSRA | LDFYQHDKVCSNTCR | 90 | 58 | 222 |
| HR7057A-44-123-Av6HT | H1FX | Q92522 | QPGKYSQLVVETIRR | GANGSFKLNRKKLEG | 80 | 59 | 223 |
| HR7299A-109-153-Av6HT | HES1 | Q14469 | KYRAGFSECMNEVTR | LLGHLANCMTQINAM | 45 | 60 | 224 |
| HR7070A-110-166-TEV | HEY2 | Q9UBP5 | GYFDAHALAMDFMSI | RLVSHLSTCATQREA | 57 | 61 | 225 |
| HR7851A-138-194-Av6HT | HHEX | Q03014 | KGGQVRFSNDQTIEL | QVKTWFQNRRAKWRR | 57 | 62 | 226 |
| HR7352A-219-295-TEV | HLF | Q16534 | IPDDLKDDKYWARRR | CKNILAKYEARHGPL | 77 | 63 | 227 |
| HR7828A-8-78-Av6HT | HMGB1 | P09429 | KPRGKMSSYAFFVQT | AKADKARYEREMKTY | 71 | 64 | 228 |
| HR7956-381-466-Av6HT | HMGXB4 | Q9UGU5 | LHTDGHSEKKKKEE | DKLIWKQKAQYLQHK | 86 | 65 | 229 |
| HR8261-201-257-Av6HT | HOXB5 | P09067 | YTRYQTLELEKEFHF | QNRRMKWKKDNKLKS | 57 | 66 | 230 |
| HR3023C-1-123-15 | HSF1 | Q00613 | MDLPVGPGAAGPSNV | EQLLENIKRKVTSVS | 123 | 67 | 231 |

FIGURE 9 (CONT.)

| Construct id | HUGO id | UniProt id | First 15 AA | Last 15 AA | Construct length | First 15 AA (SEQ ID NO) | Last 15 AA (SEQ ID NO) |
|---|---|---|---|---|---|---|---|
| HR2921-22-85-14 | ID2 | Q02363 | MISRSKTPVDDPMSL | YILDLQIALDSHPTI | 65 | 68 | 232 |
| HR3111A-32-83-15 | ID3 | Q712G9 | PAAEEPLSLLDDMNH | ILQRVIDYILDLQVV | 52 | 69 | 233 |
| HR4584C-58-112-14 | ID4 | P47928 | DEPALCLQCDMNDCY | IDYILDLQLALETHP | 55 | 70 | 234 |
| HR7614A-263-319-15 | INSM1 | Q01101 | PLGEFICQLCKEEYA | SCPANLASHRRWHKP | 57 | 71 | 235 |
| HR7614B-424-497-15 | INSM1 | Q01101 | GDGEGAGVLGLSASA | GLTRHINKCHPSENR | 74 | 72 | 236 |
| HR7043A-1-113-Av6HT | IRF2 | P14316 | MPVERMRMRPWLEEQ | IKKGNNAFRVYRMLP | 113 | 73 | 237 |
| HR7337A-9-115-TEV | IRF8 | Q02556 | RLRQWLIEQIDSSMY | LDISEPYKVYRIVPE | 107 | 74 | 238 |
| HR7553A-292-335-Av6HT | KLF1 | Q13351 | KSSHLKAHLRTHTGE | ARSDELTRHYRKHTG | 44 | 75 | 239 |
| HR8436A-125-193-Av6HT | KLF16 | Q9BXK1 | KSHRCPFPDCAKAYY | RTHTGEKRFSCPLCS | 69 | 76 | 240 |
| HR6490A-Av6HT | L3MBTL4 | Q8NA19 | MKQPNRKRKLNMDSK | SAFGCPYSDMNLKKE | 414 | 77 | 241 |
| HR6931A-209-305-Av6HT | MAFB | Q9Y5Q3 | DRFSDDQLVSMSVRE | RDAYKVKCEKLANSG | 97 | 78 | 242 |
| HR8265A-31-74-Av6HT | MAFF | Q9ULX9 | HMGLSVRELNRHLRG | KNRGYAASCRVKRVC | 46 | 79 | 243 |
| HR8110A-22-107-TEV | MAX | P61244 | ADKRAHHNALERKRR | ALLEQQVRALEKARS | 86 | 80 | 244 |
| HR8332A-280-361-TEV | MAZ | P56270 | ACEMCGKAFRDVYHL | SRPDHLNSHVRQVHS | 82 | 81 | 245 |
| HR4635D-55-161-Av6HT | MBD4 | O95243 | MIKRSSECNPLLQEP | SKRGIKSRYKDCSMA | 108 | 82 | 246 |
| HR3639F-24-96-15 | NCOA1 | Q15788 | MCDTLASSTEKRRE | RMEQEKSTTDDDVQK | 74 | 83 | 247 |
| HR4453I-100-258-Av6HT | NCOA3 | Q9Y6Q9 | VSSTGQGVIDKDSLG | SCMICVARRITTGER | 159 | 84 | 248 |
| HR4653B-214-293-14 | NFE2 | Q16621 | AKPTARGEAGSRDER | AAQNCRKRKLETIVQ | 80 | 85 | 249 |
| HR3520L-455-594-14 | NFE2L2 | Q16236 | TRDELRAKALHIPFP | EYSLQQTRDGNVFLV | 140 | 86 | 250 |
| HR3633D-248-354-Av6HT | NFKB1 | P19838 | SNLKIVRMDRTAGCV | ETSEPKPFLYYPEIK | 107 | 87 | 251 |
| HR4541D-37-329-TEV | NFKB2 | Q00653 | GPYLVIVEQPKQRGF | GDVSDSKQFTYYPLV | 293 | 88 | 252 |
| HR5518B-143-228-14 | NKX2-5 | P52952 | VLFSQAQVYELERRF | PARRIAVPVLVRDGK | 86 | 89 | 253 |
| HR6470A-132-189-15 | NKX3-1 | Q99801 | SHTQVIELERKFSHQ | RRYKTKRKQLSSELG | 58 | 90 | 254 |
| HR8303A-212-271-Av6HT | NKX3-2 | P78367 | AFSHAQVFELERRFN | RRYKTKRRQMAADLL | 60 | 91 | 255 |
| HR8155A-108-196-Av6HT | NR2C1 | P13056 | KVFDLCVVCGDKASG | SVQCERKPIEVSREK | 89 | 92 | 256 |
| HR7906B-164-410-Av6HT | NR2E3 | Q9Y5X4 | MSAARALGHHFMASL | GNTPMEKLLCDMFKN | 248 | 93 | 257 |

FIGURE 9 (CONT.)

| Construct id | HUGO id | UniProt id | First 15 AA | Last 15 AA | Construct length | First 15 AA (SEQ ID NO) | Last 15 AA (SEQ ID NO) |
|---|---|---|---|---|---|---|---|
| HR7993A-220-461-Av6HT | NR5A1 | Q13285 | GPNVPELILQLLQLE | PRNNLLIEMLQAKQT | 242 | 94 | 258 |
| HR7049C-49-159-Av6HT | NR6A1 | Q15406 | DRAEQRTCLICGDRA | SEEEIERIMSGQEFE | 111 | 95 | 259 |
| HR8346A-59-490-Av6HT | NRF1 | Q16656 | LNSTAADEVTAHLAA | AMAPVTTRISDSAVT | 432 | 96 | 260 |
| HR7010A-102-190-15 | OLIG2 | Q13516 | MTEPELQQLRLKINS | IYGGHHAGFHPSACG | 90 | 97 | 261 |
| HR7406A-210-272-Av6HT | PBX4 | Q9BYU1 | ARRKRRNFSKQATEV | SNWFGNKRIRYKKNM | 63 | 98 | 262 |
| HR7108D-342-488-Av6HT | PIKFYVE | Q9Y2I7 | TEDERKILLDSVQLK | DSDTEQIAEEGDDNL | 147 | 99 | 263 |
| HR7108D-353-488-Av6HT | PIKFYVE | Q9Y2I7 | VQLKDLWKKICHHSS | DSDTEQIAEEGDDNL | 136 | 100 | 264 |
| HR7109C-119-174-Av6HT | PLAG1 | Q6DJT9 | ETFKCEECGKNYNTK | ESTGVLLEHLKSHAG | 56 | 101 | 265 |
| HR7895A-159-199-Av6HT | PLAGL1 | Q9UM63 | DHCERCFYTRKDVRR | LCQFCAQRFGRKDHL | 41 | 102 | 266 |
| HR7815A-1736-1862-Av6HT | PLXNB1 | O43157 | NRLLREDVEYRPLTL | ALVPCLTKHVLRENQ | 126 | 103 | 267 |
| HR6946A-356-432-15 | POU3F2 | P20265 | KKRTSIEVSVKGALE | TLPGAEDVYGGSRDT | 77 | 104 | 268 |
| HR8028A-73-146-Av6HT | PPARD | Q03181 | MECRVCGDKASGFHY | KCLALGMSHNAIRFG | 75 | 105 | 269 |
| HR7923A-243-372-Av6HT | PRDM14 | Q9GZV8 | DKDSLQLPEGICLMQ | QNQELLVWYGDCYEK | 130 | 106 | 270 |
| HR8160A-72-214-Av6HT | PRDM16 | Q9HAZ2 | VYIPEDIPIPADFEL | IEPGEELLVHVKEGV | 143 | 107 | 271 |
| HR4804D-2-148-TEV | PRDM2 | Q13029 | MNQNTTEPVAATETL | EELLVWYNGEDNPEI | 148 | 108 | 272 |
| HR7077A-196-395-NHT | PRDM7 | Q9NQW5 | EPQDDDYLYCEMCQN | VNCWSGMGMSMARNW | 200 | 109 | 273 |
| HR8098A-623-689-Av6HT | PRDM8 | Q9NQV8 | AQNWCAKCNASFRMT | FRERHHLSRHMTSHN | 67 | 110 | 274 |
| HR4660B-14 | PROX1 | Q92786 | AMQEGLSPNHLKKAK | EIFKSPNCLQELLHE | 163 | 111 | 275 |
| HR7233A-95-168-Av6HT | PRRX2 | Q99811 | GSAAKRKKKQRRNRT | NRRAKFRRNERAMLA | 74 | 112 | 276 |
| HR7515B-178-423-Av6HT | RARG | P13631 | DSYELSPQLEELITK | PPLIREMLENPEMFE | 246 | 113 | 277 |
| HR7540C-653-701-Av6HT | RBAK | Q9NYW8 | CNECGKVFSQKSYLT | KFHHRSAFNSHQRIH | 49 | 114 | 278 |
| HR8007A-76-173-15 | RFX5 | P48382 | DKSSEPSTLSNEEYM | YCYSGIRRKTLVSMP | 98 | 115 | 279 |
| HR7790A-79-248-15 | RFXANK | O14593 | GNEVSALPATLDSLS | GYRKVQQVIENHILK | 170 | 116 | 280 |
| HR7107A-246-319-TEV | RNF113B | Q8IZP6 | GSEEEIPFRCFICR | KELMAKLQKLQAAEG | 74 | 117 | 281 |
| HR4563B-87-210-14 | RORA | P35398 | KEDKEVQTGYMNAQI | HRMQQQQRDHQQQPG | 124 | 118 | 282 |
| HR6875A-376-433-Av6HT | SALL4 | Q9UJQ4 | EAALYKHKCKYCSKV | FTTKGNLKVHFHRHP | 58 | 119 | 283 |

FIGURE 9 (CONT.)

| Construct id | HUGO id | UniProt id | First 15 AA | Last 15 AA | Construct length | First 15 AA (SEQ ID NO) | Last 15 AA (SEQ ID NO) |
|---|---|---|---|---|---|---|---|
| HR4435B-174-250-14 | SATB1 | Q01826 | PKLEDLPPEQWSHTT | FGRWYKHFKKTKDMM | 77 | 120 | 284 |
| HR4435E-53-178-15 | SATB1 | Q01826 | MQGVPLKHSGHLMKT | VTLKIQLHSCPKLED | 127 | 121 | 285 |
| HR4670B-55-202-Av6HT | SMAD2 | Q15796 | TGRLDELEKAITTQN | TELPPLDDYTHSIPE | 148 | 122 | 286 |
| HR4503D-314-552-Av6HT | SMAD4 | Q13485 | ISNHPAPEYWCSIAY | EVLHTMPIADPQPLD | 239 | 123 | 287 |
| HR7400B-419-538-Av6HT | SMARCC2 | Q8TAQ2 | EQTHHIIIPSYAAWF | GPPPTSHFHVLADTP | 120 | 124 | 288 |
| HR7400C-421-514-Av6HT | SMARCC2 | Q8TAQ2 | THHIIIPSYAAWFDY | VHAFLEQWGLINYQV | 94 | 125 | 289 |
| HR7811A-46-146-Av6HT | SMARCE1 | Q969G3 | GTNSRVTASSGITIP | AYHNSPAYLAYINAK | 101 | 126 | 290 |
| HR7180A-31-110-Av6HT | SOX12 | O15370 | GWCKTPSGHIKRPMN | LRLKHMADYPDYKYR | 80 | 127 | 291 |
| HR8424A-45-130-Av6HT | SOX4 | Q06945 | KADDPSWCKTPSGHI | RLKHMADYPDYKYRP | 86 | 128 | 292 |
| HR7872A-292-352-Av6HT | SP7 | Q8TDD2 | PIHSCHIPGCGKVYG | SDELERHVRTHTREK | 61 | 129 | 293 |
| HR6924A-56-131-Av6HT | SRY | Q05066 | VQDRVKRPMNAFIVW | QAMHREKYPNYKYRP | 76 | 130 | 294 |
| HR8389A-136-710-Av6HT | STAT1 | P42224 | MLDKQKELDSKVRNV | PKGTGYIKTELISVS | 576 | 131 | 295 |
| HR5539A-14 | STAT2 | P52630 | MAQWEMLQNLDSPFQ | LEEKRILIQAQRAQL | 127 | 132 | 296 |
| HR5535A-14 | STAT3 | P40763 | MAQWNQLQQLDTRYL | WEESRLLQTAATAAQ | 124 | 133 | 297 |
| HR5541B-1-127-14 | STAT5B | P51692 | MAVWIQAQQLQGEAL | LYNEQRLVREANNGS | 127 | 134 | 298 |
| HR7030-1-529-TEV | TAX1BP1 | Q86VP1 | MTSFQEVPLQTSNFA | DFDIVTKGQVCEMTK | 529 | 135 | 299 |
| HR7232A-61-248-Av6HT | TBX4 | P57082 | EQTIENIKVGLHEKE | KITQLKIENNPFAKG | 188 | 136 | 300 |
| HR8313A-52-232-Av6HT | TBX5 | Q99593 | MEGIKVFLHERELWL | QNHKITQLKIENNPF | 182 | 137 | 301 |
| HR7931A-446-500-Av6HT | TERF2 | Q15554 | KKQKWTVEESEWVKA | MIKDRWRTMKRLGMN | 55 | 138 | 302 |
| HR7939A-132-190-Av6HT | TERF2IP | Q9NYB0 | GRIAFTDADDVAILT | SWQSLKDRYLKHLRG | 59 | 139 | 303 |
| HR7501-139-450-15 | TFAP2C | Q92754 | RRDAYRRSDLLLPHA | ADSNKTLEKMEKHRK | 312 | 140 | 304 |
| HR4411B-170-232-14 | TGIF1 | Q15583 | NLPKESVQILRDWLY | ARRRLLPDMLRKDGK | 63 | 141 | 305 |
| HR7683A-320-395-Av6HT | TSC22D4 | Q9Y3Q8 | NKIEQAMDLVKSHLM | GVPRLGPPAPNGPSV | 76 | 142 | 306 |
| HR7529A-43-146-TEV | U2AF1 | Q01081 | SQTIALLNIYRNPQN | NRWFNGQPIHAELSP | 104 | 143 | 307 |
| HR6458A-220-346-15 | USF2 | Q15853 | PYSPKIDGTRTPRDE | LQQHNLEMVGEGTRQ | 127 | 144 | 308 |
| HR8032A-81-165-Av6HT | VAX2 | Q9UIW0 | VRDAKGTIREIVLPK | QNRRTKQKKDQSRDL | 85 | 145 | 309 |

FIGURE 9 (CONT.)

| Construct id | HUGO id | UniProt id | First 15 AA | Last 15 AA | Construct length | First 15 AA (SEQ ID NO) | Last 15 AA (SEQ ID NO) |
|---|---|---|---|---|---|---|---|
| HR7703A-97-158-Av6HT | VENTX | O95231 | AFTMEQVRTLEGVFQ | MKHKRQMQDPQLHSP | 62 | 146 | 310 |
| HR6940B-764-842-Av6HT | ZBTB11 | O95625 | RGYHCTQCEKSFFEA | GKEFYEKALFRRHVK | 79 | 147 | 311 |
| HR7182C-248-385-15 | ZBTB2 | Q8N680 | GSFPKYYACHLCGRR | KFIQKSHWREHMYIH | 138 | 148 | 312 |
| HR7877B-236-373-15 | ZBTB25 | P24278 | KIHLCHYCGERFDSR | PRKSQLLEHMYTHKG | 138 | 149 | 313 |
| HR7896A-1-125-Av6HT | ZBTB39 | O15060 | MGMRIKLQSTNHPNN | MEDLLQACHSTFPDL | 125 | 150 | 314 |
| HR8293A-24-183-Av6HT | ZBTB41 | Q5SVQ8 | EGNVAVECDQVTYTH | DAVKLLNNENVAPFH | 160 | 151 | 315 |
| HR8347A-1-143-Av6HT | ZBTB7B | O15156 | MGSPEDDLIGIPFPD | EIPCVIAACMEILQG | 143 | 152 | 316 |
| HR4589D-647-707-Av6HT | ZEB2 | O60315 | SPINPYKDHMSVLKA | EQRKVYQYSNSRSPS | 61 | 153 | 317 |
| HR8053A-728-784-Av6HT | ZFYVE20 | Q9H1K0 | PEAEEPIEEELLQQ | RELKHTLAKQKGGTD | 57 | 154 | 318 |
| HR7907E-658-720-Av6HT | ZHX1 | Q9UKY1 | SGSTGKICKKTPEQL | SWFGDTRYAWKNGNL | 63 | 155 | 319 |
| HR8102A-61-140-Av6HT | ZKSCAN1 | P17029 | PDPEIFRQRFRRFCY | EAVTLLEDLELDLSG | 91 | 156 | 320 |
| HR8296A-7-131-Av6HT | ZKSCAN2 | Q63HK3 | EGSDSSETFRKCFRQ | VALVVHLEKETGRLR | 96 | 157 | 321 |
| HR7446A-37-132-NHT | ZKSCAN3 | Q9BRR0 | SPDLGSEGSRERFRG | VVLLEYLERQLDEPA | 96 | 158 | 322 |
| HR8279A-12-131-Av6HT | ZNF165 | P49910 | NSPEDEGLLIVKIEE | GEEAVTILEDLERGT | 120 | 159 | 323 |
| HR8047A-6-143-Av6HT | ZNF18 | P17022 | GQALGLLPSLAKAED | WISIQVLGQDILSEK | 138 | 160 | 324 |
| HR8500A-45-132-Av6HT | ZNF192 | Q15776 | LGQEVFRLRFRQLRY | NGEEVVTLLEDLERQ | 88 | 161 | 325 |
| HR7039A-21-80-Av6HT | ZNF227 | Q86WZ6 | EAVTFKDVAVVFSRE | PFQPDMVSQLEAEEK | 60 | 162 | 326 |
| HR8056A-178-248-Av6HT | ZNF23 | P17027 | RCDSQLIQHQENNTE | SYSSHYITHQTIHSG | 71 | 163 | 327 |
| HR7779A-56-136-Av6HT | ZNF232 | Q9UNY5 | EEEQSCEYETRLPGN | LVLEQFLTILPEELQ | 81 | 164 | 328 |
| HR7401C-1-133-Av6HT | ZNF295 | Q9ULJ3 | MEGLLHYINPAHAIS | SKTPQAPFPTCPNRK | 133 | 165 | 329 |
| HR8348A-456-510-Av6HT | ZNF319 | Q9P2F9 | KPLRCTLCERRFFSS | KYASDLQRHRRVHTG | 55 | 166 | 330 |
| HR7973A-53-101-Av6HT | ZNF343 | Q6P1L6 | EGKAQIVVPVTFRDV | YKEVMLENYRNLLSL | 49 | 167 | 331 |
| HR7062-129-478-15 | ZNF410 | Q86VK4 | AGLGSSAEHLVFVQD | PQELLNQGDLTERRT | 350 | 168 | 332 |
| HR8124A-692-742-Av6HT | ZNF425 | Q6IV72 | RPFQCPECGKGFLQK | GRSFTYVGALKTHIA | 51 | 169 | 333 |
| HR8393A-22-126-Av6HT | ZNF446 | Q9NWS9 | PETARLRFRGFCYQE | LGWITAHVLKQEVLP | 105 | 170 | 334 |
| HR8114A-115-182-Av6HT | ZNF485 | Q8NCK3 | MEKGLDWEGRSSTEK | MNSSSLLNHHKVHAG | 69 | 171 | 335 |

FIGURE 9 (CONT.)

| Construct id | HUGO id | UniProt id | First 15 AA | Last 15 AA | Construct length | First 15 AA (SEQ ID NO) | Last 15 AA (SEQ ID NO) |
|---|---|---|---|---|---|---|---|
| HR8437A-468-518-Av6HT | ZNF570 | Q96NI8 | KPYECTVCGKAFSYC | KKTFRQHAHLAHHQR | 51 | 172 | 336 |
| HR8213A-490-546-Av6HT | ZNF583 | Q96ND8 | KPYECNVCGKAFSYS | RAHLAHHERIHTMES | 57 | 173 | 337 |
| HR7646A-406-485-15 | ZNF639 | Q9UID6 | DDCGKGFSSMLEYCK | NERELISHLPVHETT | 80 | 174 | 338 |
| HR7858A-251-323-Av6HT | ZNF642 | Q49AA0 | RNTYKLDLINHPTSY | SQSASLSTHQRIHTG | 73 | 175 | 339 |
| HR8203A-585-642-Av6HT | ZNF699 | Q32M78 | KPFECLECGKAFSCP | AYFRRHVKTHTRENI | 58 | 176 | 340 |
| HR7964A-390-437-Av6HT | ZNF70 | Q9UC06 | KPYTCECGKAFRHRS | LCGKSFRGSSHLIRH | 48 | 177 | 341 |
| HR8508A-34-122-Av6HT | ZNF783 | Q6ZMS7 | SYLYSTEITLWTVVA | LLQRRLENVENLLRN | 89 | 178 | 342 |
| HR8498A-486-572-Av6HT | ZNF98 | A6NK75 | GEKPYKCEECGKAFN | IAKISKYKRNCAGEK | 87 | 179 | 343 |
| HR7933A-24-120-Av6HT | ZSCAN1 | Q8NBB4 | ADPGPASPRDTEAQR | GPRSCREAASLVEDL | 93 | 180 | 344 |
| HR8495A-9-132-Av6HT | ZSCAN12 | O43309 | NNTHSREVFRQYFRQ | VTVLEDLERELDEPG | 96 | 181 | 345 |
| HR7904A-40-135-Av6HT | ZSCAN22 | P10073 | DHIAHSEAARLRFRH | AVLVEDLTQVLDKRG | 96 | 182 | 346 |
| HR8429A-9-104-Av6HT | ZSCAN29 | Q8IWY8 | ENGTNSETFRQRFRR | VTLVEDLEREPGRPR | 96 | 183 | 347 |

SEQUENCE LISTING

```
<160> NUMBER OF SEQ ID NOS: 347

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ser Gly Leu Asn Asp Ile Phe Glu Ala Gln Lys Ile Glu Trp His
1               5                   10                  15

Glu

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 2

Met Asp Val Glu Ala Trp Leu Asp Glu Arg Val Pro Leu Val Glu Thr
1               5                  10                  15

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ser Gly Leu Asn Asp Ile Phe Glu Ala Gln Lys Ile Glu Trp His
1               5                  10                  15

Glu His His His His His His Glu Asn Leu Tyr Phe Gln Ser His
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Val Glu Ala Trp Leu Asp Glu Arg Val Pro Leu Val Glu Thr
1               5                  10                  15

His His His His His His Glu Asn Leu Tyr Phe Gln Ser His
            20                  25                  30

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Glu Val Leu Phe Gln Gly Pro
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 7

His His His His His His His His
```

<210> SEQ ID NO 8
<211> LENGTH: 149
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (3)..(92)

<400> SEQUENCE: 8

```
cc atg tct ggt ctg aac gac atc ttc gaa gct cag aaa atc gaa tgg        47
   Met Ser Gly Leu Asn Asp Ile Phe Glu Ala Gln Lys Ile Glu Trp
   1               5                  10                  15 cac gaa cat cac cat cac cat cac gaa aac ctg tat ttt cag agc           92
His Glu His His His His His His Glu Asn Leu Tyr Phe Gln Ser
                20                  25                  30 catatggcga attctgcggg atcctctgag ctcggtcgac tggaagcttc tctcgag       149
```

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Ser Gly Leu Asn Asp Ile Phe Glu Ala Gln Lys Ile Glu Trp His
1               5                   10                  15

Glu His His His His His His Glu Asn Leu Tyr Phe Gln Ser
            20                  25                  30
```

<210> SEQ ID NO 10
<211> LENGTH: 166
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 10

```
ggggaauugu gagcggauaa caauuccccu cuagaaauaa uuuuguuuaa cuuuaagaag      60
gagauauacc augucugguc ugaacgacau cuucgaagcu cagaaaaucg aauggcacga     120
acaucaccau caccaucacg aaaaccugua uuuucagagc cauaug                    166
```

<210> SEQ ID NO 11
<211> LENGTH: 142
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (2)..(88)

<400> SEQUENCE: 11

```
c atg gac gtt gaa gct tgg ctg gac gaa cgt gtt ccg ctg gtt gaa acc     49
  Met Asp Val Glu Ala Trp Leu Asp Glu Arg Val Pro Leu Val Glu Thr
  1               5                   10                  15 cat cac cat cac cat cac gaa aac ctg tat ttt cag agc catatggcga        98
His His His His His His Glu Asn Leu Tyr Phe Gln Ser
```

His His His His His His Glu Asn Leu Tyr Phe Gln Ser
            20                  25 attctgcgga tcctgcgagc tctgtcgacg caaagcttct cgag           142

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Asp Val Glu Ala Trp Leu Asp Glu Arg Val Pro Leu Val Glu Thr
1               5                   10                  15

His His His His His His Glu Asn Leu Tyr Phe Gln Ser
            20                  25

<210> SEQ ID NO 13
<211> LENGTH: 163
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 13
ggggaauugu gagcggauaa caauuccccu cuagaaauaa uuuuguuuaa cuuuaagaag      60
gagauauacc auggacguug aagcuuggcu ggacgaacgu guuccgcugg uugaaaccca     120
ucaccaucac caucacgaaa accuguauuu ucagagccau aug                      163

<210> SEQ ID NO 14
<211> LENGTH: 93
<212> TYPE: DNA
<213> ORGANISM: Pyrococcus furiosus
<220> FEATURE:
<221> NAME/KEY: CDS
<222> LOCATION: (1)..(93)

<400> SEQUENCE: 14 atg agt gga tgt att ggt gga gga act aca aca cca acc caa act tcc       48
Met Ser Gly Cys Ile Gly Gly Gly Thr Thr Thr Pro Thr Gln Thr Ser
1               5                   10                  15 cct gct act caa cca acc aca aca caa act cca aca cag act gag           93
Pro Ala Thr Gln Pro Thr Thr Thr Gln Thr Pro Thr Gln Thr Glu
            20                  25                  30

<210> SEQ ID NO 15
<211> LENGTH: 31
<212> TYPE: PRT
<213> ORGANISM: Pyrococcus furiosus

<400> SEQUENCE: 15

Met Ser Gly Cys Ile Gly Gly Gly Thr Thr Thr Pro Thr Gln Thr Ser
1               5                   10                  15

Pro Ala Thr Gln Pro Thr Thr Thr Gln Thr Pro Thr Gln Thr Glu
            20                  25                  30

<210> SEQ ID NO 16
<211> LENGTH: 163
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 16

```
ggggaauugu gagcggauaa caauuccccu cuagaaauaa uuuuguuuaa cuuuaagaag    60
gagauauacc augaguggau guauuggugg aggaacuaca acaccaaccc aaacuucccc   120
ugcuacucaa ccaaccacaa cacaaacucc aacacagacu gag                     163
```

<210> SEQ ID NO 17
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(93)

<400> SEQUENCE: 17

```
atg agc ggc tgt att ggt ggt ggc acc acg acg ccg acc cag acc agc    48
Met Ser Gly Cys Ile Gly Gly Gly Thr Thr Thr Pro Thr Gln Thr Ser
1               5                   10                  15 ccg gcg acc cag ccg acc acg acc cag acc ccg acc cag acc gaa        93
Pro Ala Thr Gln Pro Thr Thr Thr Gln Thr Pro Thr Gln Thr Glu
            20                  25                  30
```

<210> SEQ ID NO 18
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Ser Gly Cys Ile Gly Gly Gly Thr Thr Thr Pro Thr Gln Thr Ser
1               5                   10                  15

Pro Ala Thr Gln Pro Thr Thr Thr Gln Thr Pro Thr Gln Thr Glu
            20                  25                  30
```

<210> SEQ ID NO 19
<211> LENGTH: 163
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19

```
ggggaauugu gagcggauaa caauuccccu cuagaaauaa uuuuguuuaa cuuuaagaag    60
gagauauacc augagcggct gtattggtgg tggcaccacg acgccgaccc agaccagccc   120
ggcgacccag ccgaccacga cccagacccc gacccagacc gaa                     163
```

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Asp Asp Glu Ser Asp Ser Gly Met Ala Ser Gln Ala Asp Gln
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Lys Ala Pro Gly Gln Pro Glu Leu Trp Asn Ala Leu Leu Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln His Val Ala Pro Pro Gly Ile Val Glu Ile Asp Ser Glu
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Asp His Gly Asp Trp Thr Tyr Glu Glu Gln Phe Lys Gln Leu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Tyr Val Tyr Glu Ser Thr Val His Cys Thr Asn Ile Leu Leu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Lys Asn Arg Ile Ala Ala Gln Lys Ser Arg Gln Arg Gln Thr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Leu Ile Leu Leu Arg Lys Thr Leu Glu Gln Leu Gln Glu Lys
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Gly Lys His Cys Arg Arg Arg Lys Ala Arg Thr Val Phe Ser
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Val Ile Lys Lys Lys Gly Glu Ile Ile Leu Trp Thr Arg
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Pro Arg Val Val Pro Asp Gln Arg Ser Lys Phe Glu Asn Glu
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Gln Val Phe Ala Ala Glu Cys Ile Leu Ser Lys Arg Leu Arg
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Lys Asp Lys Tyr Arg Val Val Tyr Thr Asp His Gln Arg Leu
1               5                   10                  15

```
<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Gly Lys Lys Ala Val Asn Lys Asp Ser Leu Glu Tyr Arg Leu
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Glu Glu Phe Glu Thr Ile Glu Arg Phe Met Asp Cys Arg Ile
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Gln Lys Asp Gly Met Val Ser Phe His Asp Asn Pro Glu Lys
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Asp Leu Gly Ile Pro Asp Leu Leu Asp Ala Trp Leu Glu Pro
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Asp Ser Lys Ser Glu Asn Gly Glu Asn Ala Pro Ile Tyr Cys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 37

Asp Ser Asn Ser Lys Ala Arg Arg Gly Ile Leu Arg Arg Ala Val
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Lys Pro Arg Thr Ile Tyr Ser Ser Tyr Gln Leu Ala Ala Leu
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Glu Ile Asn Leu Ile Leu Arg Ile Ala Glu Leu Asp Val Ala
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met His Ser His Arg Lys Arg Thr Met Phe Thr Lys Lys Gln Leu
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Ala Ser Ser Ser Gly Asn Asp Asp Asp Leu Thr Ile Pro Arg
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Ile Thr Ser Gly Ser Ser Leu Pro Asp Gly Cys Glu Gly Arg
1               5                   10                  15

<210> SEQ ID NO 43
<211> LENGTH: 15
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 43

Asp Thr Glu Arg Leu Asp Asp Phe His Leu Ser Ile His Ser Asp
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Arg Val Thr Leu Glu Val Gly Lys Val Ile Gln Gln Gly Arg
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Trp Ala Glu Asp Asn Glu Val Gln Asn Cys Met Ala Cys Gly
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Asn Tyr Glu Thr Met Gly Arg Ala Leu Arg Tyr Tyr Tyr Gln
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Asn Pro Gln Met Ser Leu Glu Gly Thr Glu Lys Ala Ser Trp
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Val Asn Ala Leu Val Ser His Leu Leu Val Val Glu Pro Glu
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Arg Leu Leu Trp Asp Tyr Val Tyr Gln Leu Leu Ser Asp Ser
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Lys Pro Pro Tyr Ser Tyr Ile Ala Leu Ile Thr Met Ala Ile
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Gly Lys Pro Arg Tyr Ser Tyr Ala Thr Leu Ile Thr Tyr Ala
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ala Glu Thr Pro Gln Lys Pro Pro Tyr Ser Tyr Ile Ala Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Ser Arg Pro Ser Ala Ser Trp Gln Asn Ser Val Ser Glu Arg
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 54

Leu Pro Pro Pro Gln Pro Gly Ala Ala Gly Gly Ser Gly Gln Pro
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ala Ser Arg Arg Val Gly Leu Ser Cys Ala Asn Cys Gln Thr
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Gly Ala Glu Glu Gly Ala Pro Val Thr Ala Gly Val Thr Ala
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Gly Ala Gly Val Lys Val Glu Ser Glu Leu Leu Cys Thr Arg
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Ala Glu Ile Val Tyr Pro Ile Thr Cys Gly Asp Ser Arg Ala
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Pro Gly Lys Tyr Ser Gln Leu Val Val Glu Thr Ile Arg Arg
1               5                   10                  15

<210> SEQ ID NO 60
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Tyr Arg Ala Gly Phe Ser Glu Cys Met Asn Glu Val Thr Arg
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Tyr Phe Asp Ala His Ala Leu Ala Met Asp Phe Met Ser Ile
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Gly Gly Gln Val Arg Phe Ser Asn Asp Gln Thr Ile Glu Leu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Pro Asp Asp Leu Lys Asp Asp Lys Tyr Trp Ala Arg Arg Arg
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Pro Arg Gly Lys Met Ser Ser Tyr Ala Phe Phe Val Gln Thr
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu His Thr Asp Gly His Ser Glu Lys Lys Lys Lys Lys Glu Glu
```

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Thr Arg Tyr Gln Thr Leu Glu Leu Glu Lys Glu Phe His Phe
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Met Asp Leu Pro Val Gly Pro Gly Ala Ala Gly Pro Ser Asn Val
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Ile Ser Arg Ser Lys Thr Pro Val Asp Asp Pro Met Ser Leu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Ala Ala Glu Glu Pro Leu Ser Leu Leu Asp Asp Met Asn His
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Glu Pro Ala Leu Cys Leu Gln Cys Asp Met Asn Asp Cys Tyr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 71

Pro Leu Gly Glu Phe Ile Cys Gln Leu Cys Lys Glu Glu Tyr Ala
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Asp Gly Glu Gly Ala Gly Val Leu Gly Leu Ser Ala Ser Ala
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Met Pro Val Glu Arg Met Arg Met Arg Pro Trp Leu Glu Glu Gln
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Leu Arg Gln Trp Leu Ile Glu Gln Ile Asp Ser Ser Met Tyr
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Ser Ser His Leu Lys Ala His Leu Arg Thr His Thr Gly Glu
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Ser His Arg Cys Pro Phe Pro Asp Cys Ala Lys Ala Tyr Tyr
1               5                   10                  15

<210> SEQ ID NO 77

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Lys Gln Pro Asn Arg Lys Arg Lys Leu Asn Met Asp Ser Lys
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Arg Phe Ser Asp Asp Gln Leu Val Ser Met Ser Val Arg Glu
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

His Met Gly Leu Ser Val Arg Glu Leu Asn Arg His Leu Arg Gly
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Asp Lys Arg Ala His His Asn Ala Leu Glu Arg Lys Arg Arg
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Cys Glu Met Cys Gly Lys Ala Phe Arg Asp Val Tyr His Leu
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82
```

```
Met Ile Lys Arg Ser Ser Glu Cys Asn Pro Leu Leu Gln Glu Pro
1               5                   10                  15
```

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

```
Met Cys Asp Thr Leu Ala Ser Ser Thr Glu Lys Arg Arg Arg Glu
1               5                   10                  15
```

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Val Ser Ser Thr Gly Gln Gly Val Ile Asp Lys Asp Ser Leu Gly
1               5                   10                  15
```

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

```
Ala Lys Pro Thr Ala Arg Gly Glu Ala Gly Ser Arg Asp Glu Arg
1               5                   10                  15
```

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Thr Arg Asp Glu Leu Arg Ala Lys Ala Leu His Ile Pro Phe Pro
1               5                   10                  15
```

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Ser Asn Leu Lys Ile Val Arg Met Asp Arg Thr Ala Gly Cys Val
1               5                   10                  15
```

<210> SEQ ID NO 88
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 88

Gly Pro Tyr Leu Val Ile Val Glu Gln Pro Lys Gln Arg Gly Phe
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Leu Phe Ser Gln Ala Gln Val Tyr Glu Leu Glu Arg Arg Phe
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser His Thr Gln Val Ile Glu Leu Glu Arg Lys Phe Ser His Gln
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Phe Ser His Ala Gln Val Phe Glu Leu Glu Arg Arg Phe Asn
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Val Phe Asp Leu Cys Val Val Cys Gly Asp Lys Ala Ser Gly
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Met Ser Ala Ala Arg Ala Leu Gly His His Phe Met Ala Ser Leu
1               5                   10                  15
```

```
<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Pro Asn Val Pro Glu Leu Ile Leu Gln Leu Leu Gln Leu Glu
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Arg Ala Glu Gln Arg Thr Cys Leu Ile Cys Gly Asp Arg Ala
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Asn Ser Thr Ala Ala Asp Glu Val Thr Ala His Leu Ala Ala
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Met Thr Glu Pro Glu Leu Gln Gln Leu Arg Leu Lys Ile Asn Ser
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Arg Arg Lys Arg Arg Asn Phe Ser Lys Gln Ala Thr Glu Val
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99
```

```
Thr Glu Asp Glu Arg Lys Ile Leu Leu Asp Ser Val Gln Leu Lys
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Val Gln Leu Lys Asp Leu Trp Lys Lys Ile Cys His His Ser Ser
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Thr Phe Lys Cys Glu Glu Cys Gly Lys Asn Tyr Asn Thr Lys
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asp His Cys Glu Arg Cys Phe Tyr Thr Arg Lys Asp Val Arg Arg
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asn Arg Leu Leu Arg Glu Asp Val Glu Tyr Arg Pro Leu Thr Leu
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Lys Arg Thr Ser Ile Glu Val Ser Val Lys Gly Ala Leu Glu
1               5                   10                  15

<210> SEQ ID NO 105
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 105

Met Glu Cys Arg Val Cys Gly Asp Lys Ala Ser Gly Phe His Tyr
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Lys Asp Ser Leu Gln Leu Pro Glu Gly Leu Cys Leu Met Gln
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Val Tyr Ile Pro Glu Asp Ile Pro Ile Pro Ala Asp Phe Glu Leu
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Met Asn Gln Asn Thr Thr Glu Pro Val Ala Ala Thr Glu Thr Leu
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Glu Pro Gln Asp Asp Asp Tyr Leu Tyr Cys Glu Met Cys Gln Asn
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Gln Asn Trp Cys Ala Lys Cys Asn Ala Ser Phe Arg Met Thr
1               5                   10                  15
```

```
<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Met Gln Glu Gly Leu Ser Pro Asn His Leu Lys Lys Ala Lys
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Ser Ala Ala Lys Arg Lys Lys Lys Gln Arg Arg Asn Arg Thr
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Ser Tyr Glu Leu Ser Pro Gln Leu Glu Glu Leu Ile Thr Lys
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Cys Asn Glu Cys Gly Lys Val Phe Ser Gln Lys Ser Tyr Leu Thr
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Lys Ser Ser Glu Pro Ser Thr Leu Ser Asn Glu Glu Tyr Met
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 116

Gly Asn Glu Val Ser Ala Leu Pro Ala Thr Leu Asp Ser Leu Ser
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Ser Glu Glu Glu Ile Pro Phe Arg Cys Phe Ile Cys Arg
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Lys Glu Asp Lys Glu Val Gln Thr Gly Tyr Met Asn Ala Gln Ile
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Glu Ala Ala Leu Tyr Lys His Lys Cys Lys Tyr Cys Ser Lys Val
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Pro Lys Leu Glu Asp Leu Pro Pro Glu Gln Trp Ser His Thr Thr
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Met Gln Gly Val Pro Leu Lys His Ser Gly His Leu Met Lys Thr
1               5                   10                  15

<210> SEQ ID NO 122
<211> LENGTH: 15
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 122

Thr Gly Arg Leu Asp Glu Leu Glu Lys Ala Ile Thr Thr Gln Asn
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile Ser Asn His Pro Ala Pro Glu Tyr Trp Cys Ser Ile Ala Tyr
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Glu Gln Thr His His Ile Ile Ile Pro Ser Tyr Ala Ala Trp Phe
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Thr His His Ile Ile Ile Pro Ser Tyr Ala Ala Trp Phe Asp Tyr
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Thr Asn Ser Arg Val Thr Ala Ser Ser Gly Ile Thr Ile Pro
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Trp Cys Lys Thr Pro Ser Gly His Ile Lys Arg Pro Met Asn
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Lys Ala Asp Asp Pro Ser Trp Cys Lys Thr Pro Ser Gly His Ile
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Pro Ile His Ser Cys His Ile Pro Gly Cys Gly Lys Val Tyr Gly
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Val Gln Asp Arg Val Lys Arg Pro Met Asn Ala Phe Ile Val Trp
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Met Leu Asp Lys Gln Lys Glu Leu Asp Ser Lys Val Arg Asn Val
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Met Ala Gln Trp Glu Met Leu Gln Asn Leu Asp Ser Pro Phe Gln
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 133

Met Ala Gln Trp Asn Gln Leu Gln Gln Leu Asp Thr Arg Tyr Leu
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Met Ala Val Trp Ile Gln Ala Gln Gln Leu Gln Gly Glu Ala Leu
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Met Thr Ser Phe Gln Glu Val Pro Leu Gln Thr Ser Asn Phe Ala
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Glu Gln Thr Ile Glu Asn Ile Lys Val Gly Leu His Glu Lys Glu
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Met Glu Gly Ile Lys Val Phe Leu His Glu Arg Glu Leu Trp Leu
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Lys Gln Lys Trp Thr Val Glu Glu Ser Glu Trp Val Lys Ala
1               5                   10                  15

<210> SEQ ID NO 139
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Arg Ile Ala Phe Thr Asp Ala Asp Asp Val Ala Ile Leu Thr
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Arg Asp Ala Tyr Arg Arg Ser Asp Leu Leu Leu Pro His Ala
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asn Leu Pro Lys Glu Ser Val Gln Ile Leu Arg Asp Trp Leu Tyr
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asn Lys Ile Glu Gln Ala Met Asp Leu Val Lys Ser His Leu Met
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Gln Thr Ile Ala Leu Leu Asn Ile Tyr Arg Asn Pro Gln Asn
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Pro Tyr Ser Pro Lys Ile Asp Gly Thr Arg Thr Pro Arg Asp Glu
```

```
1               5                   10                  15
```

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

```
Val Arg Asp Ala Lys Gly Thr Ile Arg Glu Ile Val Leu Pro Lys
1               5                   10                  15
```

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Ala Phe Thr Met Glu Gln Val Arg Thr Leu Glu Gly Val Phe Gln
1               5                   10                  15
```

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

```
Arg Gly Tyr His Cys Thr Gln Cys Glu Lys Ser Phe Phe Glu Ala
1               5                   10                  15
```

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Gly Ser Phe Pro Lys Tyr Tyr Ala Cys His Leu Cys Gly Arg Arg
1               5                   10                  15
```

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Lys Ile His Leu Cys His Tyr Cys Gly Glu Arg Phe Asp Ser Arg
1               5                   10                  15
```

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic

```
                                   peptide

<400> SEQUENCE: 150

Met Gly Met Arg Ile Lys Leu Gln Ser Thr Asn His Pro Asn Asn
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Glu Gly Asn Val Ala Val Glu Cys Asp Gln Val Thr Tyr Thr His
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Met Gly Ser Pro Glu Asp Asp Leu Ile Gly Ile Pro Phe Pro Asp
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Pro Ile Asn Pro Tyr Lys Asp His Met Ser Val Leu Lys Ala
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Pro Glu Ala Glu Glu Pro Ile Glu Glu Glu Leu Leu Leu Gln Gln
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Gly Ser Thr Gly Lys Ile Cys Lys Lys Thr Pro Glu Gln Leu
1               5                   10                  15

<210> SEQ ID NO 156
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Pro Asp Pro Glu Ile Phe Arg Gln Arg Phe Arg Arg Phe Cys Tyr
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Gly Ser Asp Ser Ser Glu Thr Phe Arg Lys Cys Phe Arg Gln
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Pro Asp Leu Gly Ser Glu Gly Ser Arg Glu Arg Phe Arg Gly
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asn Ser Pro Glu Asp Glu Gly Leu Leu Ile Val Lys Ile Glu Glu
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Gln Ala Leu Gly Leu Leu Pro Ser Leu Ala Lys Ala Glu Asp
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161
```

```
Leu Gly Gln Glu Val Phe Arg Leu Arg Phe Arg Gln Leu Arg Tyr
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Glu Ala Val Thr Phe Lys Asp Val Ala Val Phe Ser Arg Glu
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Arg Cys Asp Ser Gln Leu Ile Gln His Gln Glu Asn Asn Thr Glu
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Glu Glu Glu Gln Ser Cys Glu Tyr Glu Thr Arg Leu Pro Gly Asn
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Met Glu Gly Leu Leu His Tyr Ile Asn Pro Ala His Ala Ile Ser
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Lys Pro Leu Arg Cys Thr Leu Cys Glu Arg Arg Phe Phe Ser Ser
1               5                   10                  15

<210> SEQ ID NO 167
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 167

Glu Gly Lys Ala Gln Ile Val Val Pro Val Thr Phe Arg Asp Val
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Gly Leu Gly Ser Ser Ala Glu His Leu Val Phe Val Gln Asp
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Arg Pro Phe Gln Cys Pro Glu Cys Gly Lys Gly Phe Leu Gln Lys
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Pro Glu Thr Ala Arg Leu Arg Phe Arg Gly Phe Cys Tyr Gln Glu
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Met Glu Lys Gly Leu Asp Trp Glu Gly Arg Ser Ser Thr Glu Lys
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Lys Pro Tyr Glu Cys Thr Val Cys Gly Lys Ala Phe Ser Tyr Cys
1               5                   10                  15
```

```
<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Lys Pro Tyr Glu Cys Asn Val Cys Gly Lys Ala Phe Ser Tyr Ser
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Asp Cys Gly Lys Gly Phe Ser Ser Met Leu Glu Tyr Cys Lys
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Asn Thr Tyr Lys Leu Asp Leu Ile Asn His Pro Thr Ser Tyr
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Lys Pro Phe Glu Cys Leu Glu Cys Gly Lys Ala Phe Ser Cys Pro
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Lys Pro Tyr Thr Cys Glu Cys Gly Lys Ala Phe Arg His Arg Ser
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178
```

```
Ser Tyr Leu Tyr Ser Thr Glu Ile Thr Leu Trp Thr Val Val Ala
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Glu Lys Pro Tyr Lys Cys Glu Glu Cys Gly Lys Ala Phe Asn
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Asp Pro Gly Pro Ala Ser Pro Arg Asp Thr Glu Ala Gln Arg
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Asn Asn Thr His Ser Arg Glu Val Phe Arg Gln Tyr Phe Arg Gln
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp His Ile Ala His Ser Glu Ala Ala Arg Leu Arg Phe Arg His
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Glu Asn Gly Thr Asn Ser Glu Thr Phe Arg Gln Arg Phe Arg Arg
1               5                   10                  15

<210> SEQ ID NO 184
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 184

Leu Val Tyr Ser Ala Gly Val Tyr Arg Leu Pro Lys Asn Cys Ser
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Thr Arg Asn Glu Phe Arg Arg Phe Met Glu Lys Asn Pro Asp
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Ala Ile Pro Leu Pro Ile Gln Met Tyr Tyr Gln Gln Gln Pro
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Glu Leu Gln Ala Ala Ile Asp Ser Asn Arg Arg Glu Gly Arg Arg
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Met His Asn Leu Glu Asp Ser Cys Phe Ser Phe Leu Gln Thr Gln
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Pro Glu Val Val Tyr Ser Ala His Ala Phe His Gln Pro His Val
1               5                   10                  15
```

```
<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Ala Val Leu Arg Gln Ala Arg Arg Gln Ala Glu Lys Met Gly
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Arg Met Lys His Lys Lys Gln Leu Arg Lys Ser Gln Asp Glu Pro
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Arg Phe Gln Gln Leu Met Lys Leu Phe Glu Lys Ser Lys Cys Arg
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Met Gly Cys Leu Glu Phe Asp Glu Glu Arg Ala Gln Gln Glu
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asn Ile Leu Asp Pro Arg Leu Leu Leu Ala Phe Gln Lys Lys Glu
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 195

Arg Arg Ala Lys Glu Arg Lys Ile Asn Lys Lys Lys Leu Gln Gln
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Thr Gln Glu Leu Asp Thr Leu Arg Asn Leu Phe Arg Gln Ile Pro
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Thr Lys Arg Trp Leu Lys Asn Ala Ser Pro Glu Asp Val Glu Tyr
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Val Asn Pro Gln Phe Val Gln Lys Ser Met Gly Ser Gln Glu Asp
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ile Ala Gln Thr Ser Asn Lys Ala Ala Gln Thr Ser Thr Cys Val
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Glu Ile Arg Tyr Arg His Lys Lys Ser Arg Glu Arg Asp Gly
1               5                   10                  15

<210> SEQ ID NO 201
<211> LENGTH: 15
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 201

Val Lys Ile Trp Phe Gln Asn Arg Arg Met Lys Trp Arg Asn Ser
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gln Val Lys Ile Trp Phe Gln Asn Arg Arg Ser Lys Phe Lys Lys
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asn Ser Asn Thr Asn Ser Ser Val Gln His Val Gln Ile Arg Val
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Lys Leu Lys Lys Ala Lys Cys Lys His Ile His Gln Lys Gln
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Asn Gln Ala Gly Ser Ser Gln Asp Glu Glu Asp Asp Asp Asp Ile
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Glu Gln Cys Tyr Tyr Val Phe Gly Asp Leu Ser Gly Gly Cys
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Cys Tyr Tyr Ile Phe Gly Asp Leu Cys Gly Asn Met Ala Asn Leu
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Lys Asp Ile Gly Lys Pro Ile Glu Lys Gly Pro Arg Ala Lys
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Lys Pro Val Arg Val Cys Asp Ala Cys Phe Asn Asp Leu Gln Gly
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Val Ala Arg Val Val Asn Ile Thr Ser Pro Gly His Asp Ala
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Asp Gln Leu His Ala Gln Leu Arg Asp Leu Thr Ser Ser Ser
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 212

Pro Met His Lys Leu Phe Leu Glu Met Leu Glu Ala Met Met Asp
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Arg Thr Asp Arg Leu Glu His Leu Glu Ser Gln Glu Leu Asp
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Glu Asp Met Phe Asp Asn Gly Ser Phe Leu Arg Arg Arg Lys Arg
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Tyr Trp Thr Ile Asp Thr Cys Pro Asp Ile Ser Arg Lys Arg Arg
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Leu Asp Pro Arg Cys Leu Asp Met Phe Glu Asn Gly Asn Tyr Arg
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asn Pro Glu Leu Arg Arg Asn Met Thr Ile Lys Thr Glu Leu Pro
1               5                   10                  15

<210> SEQ ID NO 218
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Asn Lys Tyr Thr Lys Ser Arg Gly Arg Ala Ala Lys Lys Lys Ala
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Pro Leu Ala Met Arg Lys Glu Gly Ile Gln Thr Arg Lys Arg Lys
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gln Asn Arg Arg Ala Lys Trp Lys Arg Ile Lys Ala Gly Asn Val
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gln His Lys Ala Val His Ser Gln Glu Arg Ser Phe Asp Cys Lys
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Leu Asp Phe Tyr Gln His Asp Lys Val Cys Ser Asn Thr Cys Arg
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Ala Asn Gly Ser Phe Lys Leu Asn Arg Lys Lys Leu Glu Gly
```

```
1               5                   10                  15
```

<210> SEQ ID NO 224
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

```
Leu Leu Gly His Leu Ala Asn Cys Met Thr Gln Ile Asn Ala Met
1               5                   10                  15
```

<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

```
Arg Leu Val Ser His Leu Ser Thr Cys Ala Thr Gln Arg Glu Ala
1               5                   10                  15
```

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

```
Gln Val Lys Thr Trp Phe Gln Asn Arg Arg Ala Lys Trp Arg Arg
1               5                   10                  15
```

<210> SEQ ID NO 227
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

```
Cys Lys Asn Ile Leu Ala Lys Tyr Glu Ala Arg His Gly Pro Leu
1               5                   10                  15
```

<210> SEQ ID NO 228
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

```
Ala Lys Ala Asp Lys Ala Arg Tyr Glu Arg Glu Met Lys Thr Tyr
1               5                   10                  15
```

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 229

Asp Lys Leu Ile Trp Lys Gln Lys Ala Gln Tyr Leu Gln His Lys
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gln Asn Arg Arg Met Lys Trp Lys Lys Asp Asn Lys Leu Lys Ser
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Glu Gln Leu Leu Glu Asn Ile Lys Arg Lys Val Thr Ser Val Ser
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Tyr Ile Leu Asp Leu Gln Ile Ala Leu Asp Ser His Pro Thr Ile
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ile Leu Gln Arg Val Ile Asp Tyr Ile Leu Asp Leu Gln Val Val
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ile Asp Tyr Ile Leu Asp Leu Gln Leu Ala Leu Glu Thr His Pro
1               5                   10                  15

<210> SEQ ID NO 235

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Cys Pro Ala Asn Leu Ala Ser His Arg Arg Trp His Lys Pro
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Leu Thr Arg His Ile Asn Lys Cys His Pro Ser Glu Asn Arg
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ile Lys Lys Gly Asn Asn Ala Phe Arg Val Tyr Arg Met Leu Pro
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Leu Asp Ile Ser Glu Pro Tyr Lys Val Tyr Arg Ile Val Pro Glu
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Arg Ser Asp Glu Leu Thr Arg His Tyr Arg Lys His Thr Gly
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240
```

```
Arg Thr His Thr Gly Glu Lys Arg Phe Ser Cys Pro Leu Cys Ser
1               5                   10                  15
```

<210> SEQ ID NO 241
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

```
Ser Ala Phe Gly Cys Pro Tyr Ser Asp Met Asn Leu Lys Lys Glu
1               5                   10                  15
```

<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

```
Arg Asp Ala Tyr Lys Val Lys Cys Glu Lys Leu Ala Asn Ser Gly
1               5                   10                  15
```

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

```
Lys Asn Arg Gly Tyr Ala Ala Ser Cys Arg Val Lys Arg Val Cys
1               5                   10                  15
```

<210> SEQ ID NO 244
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Ala Leu Leu Glu Gln Gln Val Arg Ala Leu Glu Lys Ala Arg Ser
1               5                   10                  15
```

<210> SEQ ID NO 245
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

```
Ser Arg Pro Asp His Leu Asn Ser His Val Arg Gln Val His Ser
1               5                   10                  15
```

<210> SEQ ID NO 246
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 246

Ser Lys Arg Gly Ile Lys Ser Arg Tyr Lys Asp Cys Ser Met Ala
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Arg Met Glu Gln Glu Lys Ser Thr Thr Asp Asp Val Gln Lys
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ser Cys Met Ile Cys Val Ala Arg Arg Ile Thr Thr Gly Glu Arg
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Ala Gln Asn Cys Arg Lys Arg Lys Leu Glu Thr Ile Val Gln
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Glu Tyr Ser Leu Gln Gln Thr Arg Asp Gly Asn Val Phe Leu Val
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Glu Thr Ser Glu Pro Lys Pro Phe Leu Tyr Tyr Pro Glu Ile Lys
1               5                   10                  15
```

```
<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Asp Val Ser Asp Ser Lys Gln Phe Thr Tyr Tyr Pro Leu Val
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Pro Ala Arg Arg Ile Ala Val Pro Val Leu Val Arg Asp Gly Lys
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Arg Arg Tyr Lys Thr Lys Arg Lys Gln Leu Ser Ser Glu Leu Gly
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Arg Arg Tyr Lys Thr Lys Arg Arg Gln Met Ala Ala Asp Leu Leu
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ser Val Gln Cys Glu Arg Lys Pro Ile Glu Val Ser Arg Glu Lys
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257
```

```
Gly Asn Thr Pro Met Glu Lys Leu Leu Cys Asp Met Phe Lys Asn
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Pro Arg Asn Asn Leu Leu Ile Glu Met Leu Gln Ala Lys Gln Thr
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ser Glu Glu Glu Ile Glu Arg Ile Met Ser Gly Gln Glu Phe Glu
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ala Met Ala Pro Val Thr Thr Arg Ile Ser Asp Ser Ala Val Thr
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ile Tyr Gly Gly His His Ala Gly Phe His Pro Ser Ala Cys Gly
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ser Asn Trp Phe Gly Asn Lys Arg Ile Arg Tyr Lys Lys Asn Met
1               5                   10                  15

<210> SEQ ID NO 263
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 263

Asp Ser Asp Thr Glu Gln Ile Ala Glu Glu Gly Asp Asp Asn Leu
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Asp Ser Asp Thr Glu Gln Ile Ala Glu Glu Gly Asp Asp Asn Leu
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Glu Ser Thr Gly Val Leu Leu Glu His Leu Lys Ser His Ala Gly
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Leu Cys Gln Phe Cys Ala Gln Arg Phe Gly Arg Lys Asp His Leu
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ala Leu Val Pro Cys Leu Thr Lys His Val Leu Arg Glu Asn Gln
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Thr Leu Pro Gly Ala Glu Asp Val Tyr Gly Gly Ser Arg Asp Thr
1               5                   10                  15
```

```
<210> SEQ ID NO 269
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Lys Cys Leu Ala Leu Gly Met Ser His Asn Ala Ile Arg Phe Gly
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Asn Gln Glu Leu Leu Val Trp Tyr Gly Asp Cys Tyr Glu Lys
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ile Glu Pro Gly Glu Glu Leu Leu Val His Val Lys Glu Gly Val
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Glu Glu Leu Leu Val Trp Tyr Asn Gly Glu Asp Asn Pro Glu Ile
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Val Asn Cys Trp Ser Gly Met Gly Met Ser Met Ala Arg Asn Trp
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 274

Phe Arg Glu Arg His His Leu Ser Arg His Met Thr Ser His Asn
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Glu Ile Phe Lys Ser Pro Asn Cys Leu Gln Glu Leu Leu His Glu
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Asn Arg Arg Ala Lys Phe Arg Arg Asn Glu Arg Ala Met Leu Ala
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Pro Pro Leu Ile Arg Glu Met Leu Glu Asn Pro Glu Met Phe Glu
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Lys Phe His His Arg Ser Ala Phe Asn Ser His Gln Arg Ile His
1               5                   10                  15

<210> SEQ ID NO 279
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Tyr Cys Tyr Ser Gly Ile Arg Arg Lys Thr Leu Val Ser Met Pro
1               5                   10                  15

<210> SEQ ID NO 280
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 280

Gly Tyr Arg Lys Val Gln Gln Val Ile Glu Asn His Ile Leu Lys
1               5                   10                  15

<210> SEQ ID NO 281
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Lys Glu Leu Met Ala Lys Leu Gln Lys Leu Gln Ala Ala Glu Gly
1               5                   10                  15

<210> SEQ ID NO 282
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

His Arg Met Gln Gln Gln Gln Arg Asp His Gln Gln Gln Pro Gly
1               5                   10                  15

<210> SEQ ID NO 283
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Phe Thr Thr Lys Gly Asn Leu Lys Val His Phe His Arg His Pro
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Phe Gly Arg Trp Tyr Lys His Phe Lys Thr Lys Asp Met Met
1               5                   10                  15

<210> SEQ ID NO 285
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Val Thr Leu Lys Ile Gln Leu His Ser Cys Pro Lys Leu Glu Asp
1               5                   10                  15
```

<210> SEQ ID NO 286
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Thr Glu Leu Pro Pro Leu Asp Asp Tyr Thr His Ser Ile Pro Glu
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Glu Val Leu His Thr Met Pro Ile Ala Asp Pro Gln Pro Leu Asp
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gly Pro Pro Pro Thr Ser His Phe His Val Leu Ala Asp Thr Pro
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Val His Ala Phe Leu Glu Gln Trp Gly Leu Ile Asn Tyr Gln Val
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Tyr His Asn Ser Pro Ala Tyr Leu Ala Tyr Ile Asn Ala Lys
1               5                   10                  15

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Leu Arg Leu Lys His Met Ala Asp Tyr Pro Asp Tyr Lys Tyr Arg
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Arg Leu Lys His Met Ala Asp Tyr Pro Asp Tyr Lys Tyr Arg Pro
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ser Asp Glu Leu Glu Arg His Val Arg Thr His Thr Arg Glu Lys
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gln Ala Met His Arg Glu Lys Tyr Pro Asn Tyr Lys Tyr Arg Pro
1               5                   10                  15

<210> SEQ ID NO 295
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Pro Lys Gly Thr Gly Tyr Ile Lys Thr Glu Leu Ile Ser Val Ser
1               5                   10                  15

<210> SEQ ID NO 296
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Leu Glu Glu Lys Arg Ile Leu Ile Gln Ala Gln Arg Ala Gln Leu
1               5                   10                  15

<210> SEQ ID NO 297
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Trp Glu Glu Ser Arg Leu Leu Gln Thr Ala Ala Thr Ala Ala Gln
1               5                   10                  15

<210> SEQ ID NO 298
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Leu Tyr Asn Glu Gln Arg Leu Val Arg Glu Ala Asn Asn Gly Ser
1               5                   10                  15

<210> SEQ ID NO 299
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Asp Phe Asp Ile Val Thr Lys Gly Gln Val Cys Glu Met Thr Lys
1               5                   10                  15

<210> SEQ ID NO 300
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Lys Ile Thr Gln Leu Lys Ile Glu Asn Asn Pro Phe Ala Lys Gly
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gln Asn His Lys Ile Thr Gln Leu Lys Ile Glu Asn Asn Pro Phe
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Met Ile Lys Asp Arg Trp Arg Thr Met Lys Arg Leu Gly Met Asn
```

```
                1               5                  10                 15
```

<210> SEQ ID NO 303
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

```
Ser Trp Gln Ser Leu Lys Asp Arg Tyr Leu Lys His Leu Arg Gly
1               5                  10                 15
```

<210> SEQ ID NO 304
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

```
Ala Asp Ser Asn Lys Thr Leu Glu Lys Met Glu Lys His Arg Lys
1               5                  10                 15
```

<210> SEQ ID NO 305
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

```
Ala Arg Arg Arg Leu Leu Pro Asp Met Leu Arg Lys Asp Gly Lys
1               5                  10                 15
```

<210> SEQ ID NO 306
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

```
Gly Val Pro Arg Leu Gly Pro Pro Ala Pro Asn Gly Pro Ser Val
1               5                  10                 15
```

<210> SEQ ID NO 307
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

```
Asn Arg Trp Phe Asn Gly Gln Pro Ile His Ala Glu Leu Ser Pro
1               5                  10                 15
```

<210> SEQ ID NO 308
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Leu Gln Gln His Asn Leu Glu Met Val Gly Glu Gly Thr Arg Gln
1               5                   10                  15

<210> SEQ ID NO 309
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gln Asn Arg Arg Thr Lys Gln Lys Lys Asp Gln Ser Arg Asp Leu
1               5                   10                  15

<210> SEQ ID NO 310
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Met Lys His Lys Arg Gln Met Gln Asp Pro Gln Leu His Ser Pro
1               5                   10                  15

<210> SEQ ID NO 311
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Lys Glu Phe Tyr Glu Lys Ala Leu Phe Arg Arg His Val Lys
1               5                   10                  15

<210> SEQ ID NO 312
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Lys Phe Ile Gln Lys Ser His Trp Arg Glu His Met Tyr Ile His
1               5                   10                  15

<210> SEQ ID NO 313
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Pro Arg Lys Ser Gln Leu Leu Glu His Met Tyr Thr His Lys Gly
1               5                   10                  15

<210> SEQ ID NO 314

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Met Glu Asp Leu Leu Gln Ala Cys His Ser Thr Phe Pro Asp Leu
1               5                   10                  15

<210> SEQ ID NO 315
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asp Ala Val Lys Leu Leu Asn Asn Glu Asn Val Ala Pro Phe His
1               5                   10                  15

<210> SEQ ID NO 316
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Glu Ile Pro Cys Val Ile Ala Ala Cys Met Glu Ile Leu Gln Gly
1               5                   10                  15

<210> SEQ ID NO 317
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Glu Gln Arg Lys Val Tyr Gln Tyr Ser Asn Ser Arg Ser Pro Ser
1               5                   10                  15

<210> SEQ ID NO 318
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Arg Glu Leu Lys His Thr Leu Ala Lys Gln Lys Gly Gly Thr Asp
1               5                   10                  15

<210> SEQ ID NO 319
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319
```

```
Ser Trp Phe Gly Asp Thr Arg Tyr Ala Trp Lys Asn Gly Asn Leu
1               5                   10                  15

<210> SEQ ID NO 320
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Glu Ala Val Thr Leu Leu Glu Asp Leu Glu Leu Asp Leu Ser Gly
1               5                   10                  15

<210> SEQ ID NO 321
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Val Ala Leu Val Val His Leu Glu Lys Glu Thr Gly Arg Leu Arg
1               5                   10                  15

<210> SEQ ID NO 322
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Val Val Leu Leu Glu Tyr Leu Glu Arg Gln Leu Asp Glu Pro Ala
1               5                   10                  15

<210> SEQ ID NO 323
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Gly Glu Glu Ala Val Thr Ile Leu Glu Asp Leu Glu Arg Gly Thr
1               5                   10                  15

<210> SEQ ID NO 324
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Trp Ile Ser Ile Gln Val Leu Gly Gln Asp Ile Leu Ser Glu Lys
1               5                   10                  15

<210> SEQ ID NO 325
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 325

Asn Gly Glu Glu Val Val Thr Leu Leu Glu Asp Leu Glu Arg Gln
1               5                   10                  15

<210> SEQ ID NO 326
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Pro Phe Gln Pro Asp Met Val Ser Gln Leu Glu Ala Glu Glu Lys
1               5                   10                  15

<210> SEQ ID NO 327
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Ser Tyr Ser Ser His Tyr Ile Thr His Gln Thr Ile His Ser Gly
1               5                   10                  15

<210> SEQ ID NO 328
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Leu Val Leu Glu Gln Phe Leu Thr Ile Leu Pro Glu Glu Leu Gln
1               5                   10                  15

<210> SEQ ID NO 329
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Ser Lys Thr Pro Gln Ala Pro Phe Pro Thr Cys Pro Asn Arg Lys
1               5                   10                  15

<210> SEQ ID NO 330
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Lys Tyr Ala Ser Asp Leu Gln Arg His Arg Arg Val His Thr Gly
1               5                   10                  15
```

```
<210> SEQ ID NO 331
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Tyr Lys Glu Val Met Leu Glu Asn Tyr Arg Asn Leu Leu Ser Leu
1               5                   10                  15

<210> SEQ ID NO 332
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Pro Gln Glu Leu Leu Asn Gln Gly Asp Leu Thr Glu Arg Arg Thr
1               5                   10                  15

<210> SEQ ID NO 333
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gly Arg Ser Phe Thr Tyr Val Gly Ala Leu Lys Thr His Ile Ala
1               5                   10                  15

<210> SEQ ID NO 334
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Leu Gly Trp Ile Thr Ala His Val Leu Lys Gln Glu Val Leu Pro
1               5                   10                  15

<210> SEQ ID NO 335
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Met Asn Ser Ser Ser Leu Leu Asn His His Lys Val His Ala Gly
1               5                   10                  15

<210> SEQ ID NO 336
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336
```

```
Lys Lys Thr Phe Arg Gln His Ala His Leu Ala His His Gln Arg
1               5                   10                  15

<210> SEQ ID NO 337
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Arg Ala His Leu Ala His His Glu Arg Ile His Thr Met Glu Ser
1               5                   10                  15

<210> SEQ ID NO 338
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Asn Glu Arg Glu Leu Ile Ser His Leu Pro Val His Glu Thr Thr
1               5                   10                  15

<210> SEQ ID NO 339
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ser Gln Ser Ala Ser Leu Ser Thr His Gln Arg Ile His Thr Gly
1               5                   10                  15

<210> SEQ ID NO 340
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Ala Tyr Phe Arg Arg His Val Lys Thr His Thr Arg Glu Asn Ile
1               5                   10                  15

<210> SEQ ID NO 341
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Leu Cys Gly Lys Ser Phe Arg Gly Ser Ser His Leu Ile Arg His
1               5                   10                  15

<210> SEQ ID NO 342
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 342

Leu Leu Gln Arg Arg Leu Glu Asn Val Glu Asn Leu Leu Arg Asn
1               5                   10                  15

<210> SEQ ID NO 343
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ile Ala Lys Ile Ser Lys Tyr Lys Arg Asn Cys Ala Gly Glu Lys
1               5                   10                  15

<210> SEQ ID NO 344
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gly Pro Arg Ser Cys Arg Glu Ala Ala Ser Leu Val Glu Asp Leu
1               5                   10                  15

<210> SEQ ID NO 345
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Val Thr Val Leu Glu Asp Leu Glu Arg Glu Leu Asp Glu Pro Gly
1               5                   10                  15

<210> SEQ ID NO 346
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ala Val Leu Val Glu Asp Leu Thr Gln Val Leu Asp Lys Arg Gly
1               5                   10                  15

<210> SEQ ID NO 347
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Val Thr Leu Val Glu Asp Leu Glu Arg Glu Pro Gly Arg Pro Arg
1               5                   10                  15
```

TRANSCRIPT OPTIMIZED EXPRESSION ENHANCEMENT FOR HIGH-LEVEL PRODUCTION OF PROTEINS AND PROTEIN DOMAINS

CROSS-REFERENCE TO RELATED APPLICATION(S)

This application is a continuation of U.S. application Ser. No. 14/357,484, which is a 35 U.S.C. § 371 application of International Application Serial No. PCT/US2012/064836, filed Nov. 13, 2012, which claims the benefit of U.S. Provisional Application Ser. No. 61/558,277, filed Nov. 10, 2011. The entire content of the applications referenced above are hereby incorporated by reference herein.

STATEMENT OF GOVERNMENT SUPPORT

This invention was made with government support under U54-GM074958 awarded by the National Institute of General Medical Sciences Protein Structure Initiative and U01-DC011485 awarded by the National Institute on Deafness and other Communication Disorders under the auspices of the NIH Common Fund. The government has certain rights in the invention.

SEQUENCE LISTING

The instant application contains a Sequence Listing which has been submitted electronically in ASCII format and is hereby incorporated by reference in its entirety. Said ASCII copy, created on Mar. 24, 2016, is named 08035.047US2_SL.txt and is 99,081 bytes in size.

BACKGROUND

The production of recombinant proteins and protein domains as reagents is extremely valuable to biomedical researchers and the entire biotechnology industry. *Escherichia coli* expression systems are the most cost effective and widely utilized expression systems for this task. However, production of certain proteins can be challenging in this bacterial system. Often proteins or protein domains fail to express at sufficient levels to allow for the purification of the protein reagents. This is especially true of the protein coding sequences derived from higher eukaryotes (such as humans). For example, using a standard pET *E. coli* expression system (Acton et al., 2011), nearly one-third of human protein targets produced in a large scale screen of protein expression had no detectable expression levels.

Thus, there is a need for agents and methods for high-level production of recombinant proteins and protein domains that do not require RNA optimization for each individual target gene.

SUMMARY OF CERTAIN EMBODIMENTS OF THE INVENTION

This invention relates to a system for high-level production of recombinant proteins and protein domains that does not require RNA optimization for each individual target gene.

Certain embodiments of the invention provide a method of preparing an expression vector, wherein the expression vector comprises, in order of position: a first nucleic acid sequence encoding a 5' untranslated region of an expressed mRNA that comprises a ribosome binding site (RBS); a second nucleic acid sequence encoding a polypeptide tag; and a cloning site, wherein the cloning site enables a target protein coding sequence to be inserted into the vector in-frame with the second nucleic acid sequence to encode a fusion protein comprising the polypeptide tag and the target protein; and wherein the method comprises specifically modifying the nucleic acid sequence encoding (i) the 5' untranslated region and (ii) the adjacent polypeptide tag to minimize RNA secondary structure both within and/or between these two regions of the mRNA.

Certain embodiments of the invention provide an expression vector designed using the methods described herein.

Certain embodiments of the invention provide an expression vector comprising, in order of position: a first nucleic acid sequence encoding a 5' untranslated region of an expressed mRNA that comprises a ribosome binding site (RBS); a second nucleic acid sequence encoding a polypeptide tag; and a cloning site, wherein the cloning site enables a target protein coding sequence to be inserted into the vector in-frame with the second nucleic acid sequence to encode a fusion protein comprising the polypeptide tag and the target protein; and wherein the nucleic acid sequence encoding (i) the 5' untranslated region and (ii) the adjacent polypeptide tag has been specifically modified to minimize RNA secondary structure both within and/or between these two regions of the mRNA.

Certain embodiments of the invention provide a host cell comprising an expression vector as described herein.

The details of one or more embodiments of the invention are set forth in the description below. Other features, objects, and advantages of the invention will be apparent from the description and from the claims.

BRIEF DESCRIPTION OF THE DRAWINGS

FIG. 8. Expression Results for Select Target Proteins. E=Expression; E=0-5 (no to high expression). S=Solubility; S=0 - 5 (no to high solubility). ES=E*S=(0 - 25) ES≥9 usability (boxed numbers). ES≥9 (typically results in ≥5 milligrams of protein per one liter of *E. coli* Fermentation).

FIG. 9. Human transcription factor protein and domain constructs designed using the NESG Construct Optimization Software for production using TOEET technologies. Each line in the table describes a unique protein construct for RT-PCR cloning, defined by the NESG Vector ID, the HUGO protein identifier, the Uniprot protein identifier, the first 15 amino acid residues in the targeted construct, the last 15 amino acid residues in the target construct, and the length of the targeted gene. The actual length of the targeted gene obtained by RT-PCR may be shorter or longer than indicated in the table due RNA spicing variations.

Figure 1:
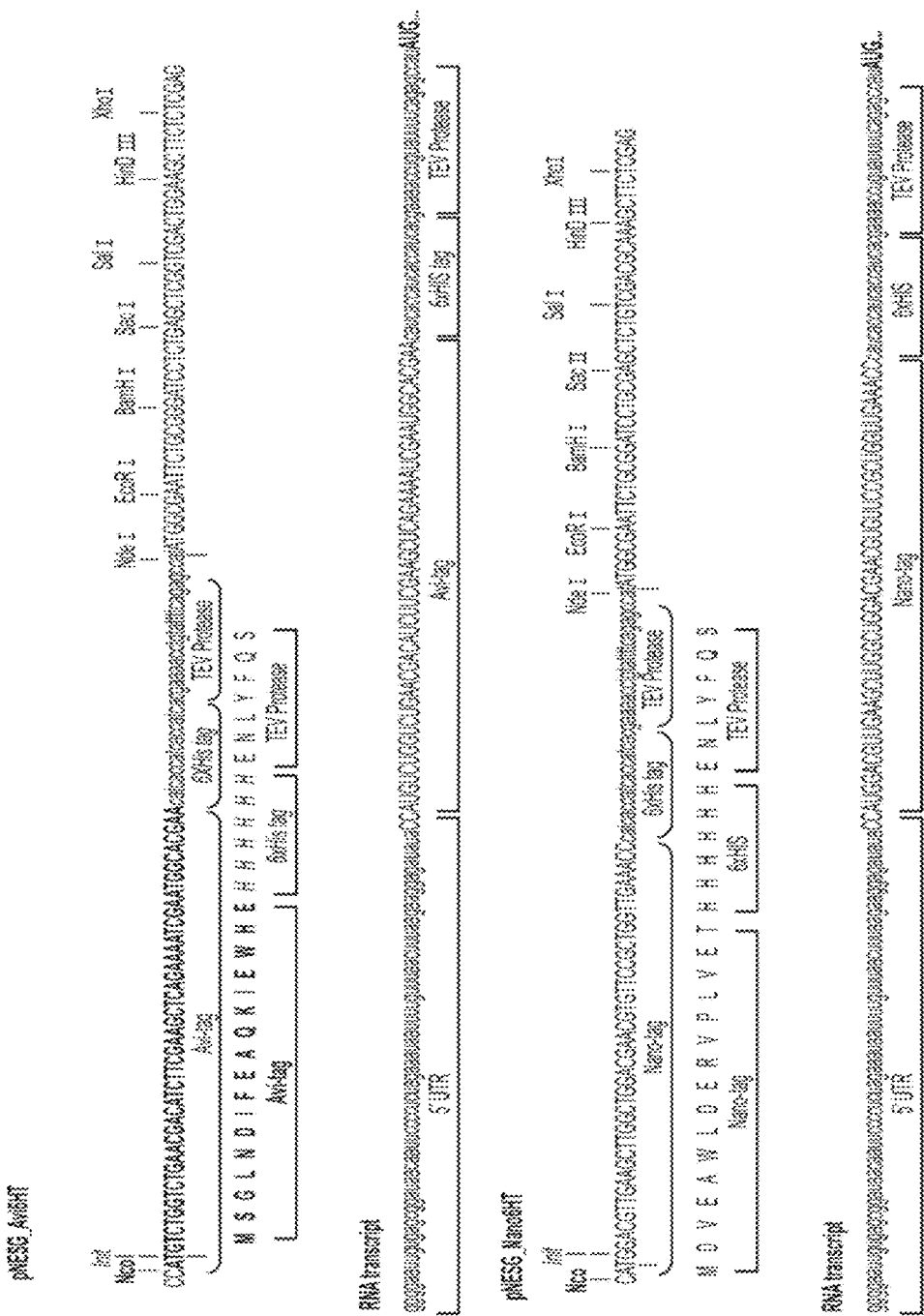
FIG. 1 is a set of diagrams showing sequences of Avi-tag and Nano-tag based Transcript-Optimized Expression Enhancement Technology (TOEET) expression vectors. The pNESG_Avi6HT Avi-tag sequence (top) (DNA, RNA and protein sequence), the His-tag sequences and the TEV Protease Recognition Site sequences are shown as indicated. Similarly, for pNESG_Nano6HT (bottom) the Nano-tag sequences, the His-tag sequences and TEV Protease Recognition Site sequences are shown as indicated. The T7 RNA transcript produced by each vector is shown under each vector with untranslated sequences indicated with brackets. The Multiple Cloning Site (MCS) is also shown after the tag sequences, including the positions and identity of restriction sites available for cloning. Figure discloses "6×His" as SEQ ID NO: 5, as well as SEQ ID NOS 8-13, respectively, in order of appearance.

DETAILED DESCRIPTION mRNA stem-loop structures often inhibit translation initiation and therefore reduce recombinant protein expression (Nomura et al., 1984). High level expression of proteins is affected by a lack of mRNA secondary structure near the translation start site (Kudla et al., 2009; Rocha et al., 1999). In addition, rare codons present within the first ten residues of a protein have deleterious effects on protein expression levels (Gonzalez de Valdivia and Isaksson, 2004). *E. coli*, like all organisms, prefers to use a subset of the possible codons. The codons that an organism utilizes only infrequently are termed "rare codons" of that organism.

Heterologous genes from other organisms, which generally have a different codon bias, often contain *E. coli* rare codons. Decreasing or minimizing mRNA secondary structure near the Ribosome Binding Site (RBS) and translation initiation site, and separately that a lack of rare codons near the start of translation, are important for high level *E. coli* protein expression (Gonzalez de Valdivia and Isaksson, 2004; Kudla et al., 2009). However, the DNA coding sequence of a target gene destined for heterologous expression in *E. coli* has evolved under different conditions and may intrinsically contain deleterious rare codons and mRNA secondary structure when cloned into an expression vector. Deleterious rare codons and mRNA secondary structure features are particularly problematic when expressing domains or specific segments of target proteins; e.g., gene segments coding for fragments other than the native N-terminal region of the protein have not evolved to provide for efficient translation initiation. Total gene synthesis, or the chemical synthesis of a protein coding region, may address these problems to some extent, since the DNA sequence can be optimized to reduce these issues (Quan et al., 2011). However, the costs of total gene synthesis are prohibitive for large sets of protein targets, and generally is not suitable for large-scale screening or projects involving expression of many different proteins.

This invention is based, at least in part, on an unexpected discovery of a new methodology for achieving high-level production of recombinant proteins and protein domains. RNA sequence optimization is a well-known approach for improving protein expression. A feature of the system described herein is that RNA sequence optimization is required only in DNA comprising the vector backbone, including the DNA coding for the 5'-UTR and a common N-terminal polypeptide tag. Each target gene, coding for various target proteins, that is cloned into this vector backbone, need not be optimized individually. Hence, the optimized vector backbone can be used to enhance expression of many different target proteins without the need for target-protein-specific gene sequence optimization. Unlike certain previous methods, gene-by-gene RNA transcript sequence optimization is not required in certain embodiments of the methods described herein. The methodology includes, among others, jointly designing and optimizing sequences encoding 5' untranslated and 5' translated regions of the mRNA transcript produced by an expression vector so as to minimize RNA secondary structure and/or optimize codon usage in the mRNA transcript.

In one aspect, this invention addresses, among others, the problems associated with mRNA secondary structure and codon bias. Accordingly, the invention provides systems for high-level production of recombinant proteins and protein domains based on the Transcript-Optimized Expression Enhancement Technology (TOEET). As disclosed herein, TOEET is used to design expression vectors that produce mRNA transcripts with minimal RNA secondary structure and optimum codon usage in the nucleotide region around the Ribosomal Binding Site (RBS) and the translation initiation site, as well as minimal RNA secondary structure and optimal codon usage in a region of the transcript coding for an N-terminal polypeptide tag that is encoded directly downstream of the translation initiation site. Optimization can extend up to approximately 100 or more nucleotides on each of the 5' and 3' sides of the RBS. This generally will involve producing a protein with an N-terminal polypeptide tag, which is called an Expression Enhancement Tag (EET). This EET may be designed with other features that support protein production, such as solubility enhancing properties or affinity purification sequence motifs. Solubility enhancing tags known from the literature include the maltose-binding protein, the B1 domain of protein G, and domain of myxococcus protein S, to name a few representative examples. Expression vectors designed with TOEET allow most genes of interest to be produced with enhanced expression.

An advantage of the TOEET strategy over target gene optimization by total gene synthesis is that unless the 5' end of the synthetic gene is optimized in the context of the untranslated vector sequences, detrimental mRNA secondary structure may form near or around the RBS/translation initiation site. More specifically, even if the 5' translated region of the target gene is optimized by gene synthesis or by specific mutations, enhanced expression may not be realized unless the 5'-translated and 5'-untranslated regions of the transcript are jointly optimized, as described herein. Furthermore, by using a sufficiently long N-terminal EET tag, translated from an optimized RNA sequence that is encoded by the vector itself, there is no need to optimize the sequence of the target gene, avoiding the need for gene-specific synthesis or modification. This feature allows the TOEET technology to be used for target protein expression enhancement in high throughput applications, including expression screening studies and projects involving expression of many different proteins, where gene-specific synthesis or modification would be costly or impractical. The roughly 30 amino-acid residue (or larger) EETs effectively shift any deleterious RNA features of the target gene transcript significantly downstream of the RBS/translation initiation site, so that any potential RNA secondary structure formation with the 5' end of the transcript is avoided, and any RNA secondary structure within the RNA coded for by the target gene itself will likely have little or no effect on expression. This TOEET strategy, which is independent of the target gene sequence, could be used more generally to enhance the expression levels of proteins produced with almost any expression vector or system.

Accordingly, certain embodiments of the invention provide a method of preparing an expression vector, wherein the expression vector comprises, in order of position: a first nucleic acid sequence encoding a 5' untranslated region (UTR) of an expressed mRNA that comprises a ribosome binding site (RBS); a second nucleic acid sequence encoding a polypeptide tag (i.e., at the N-terminal end of the expressed target protein); and a cloning site, wherein the cloning site enables a target protein coding sequence to be inserted into the vector in-frame with the second nucleic acid sequence to encode a fusion protein comprising the polypeptide tag and the target protein; and wherein the method comprises specifically modifying the nucleic acid sequence encoding (i) the 5' untranslated region and (ii) the adjacent polypeptide tag to minimize RNA secondary structure both within and/or between these two regions of the mRNA.

As used herein, a vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, repressor binding sites, and other expression control elements (e.g., polyadenylation signals). Regulatory sequences include those that direct constitutive expression of a nucleotide sequence, as well as tissue-specific regulatory and/or inducible sequences. For example, in certain embodiments of the invention, an expression vector described herein comprises a 5' upstream sequence encoding an operable promoter and associated regulatory sequences. The design of the expression vector can depend on such factors as the choice of the host cell to be transformed, the level of expression of protein desired, and the like.

As used herein, the 5'UTR of the encoded messenger RNA is transcribed from a promoter and includes a ribosome binding site several nucleotides preceding the start codon.

As used herein, a "cloning site" enables a sequence, such as, e.g., a target protein coding sequence, to be inserted into an expression vector. For example, the cloning site may be a multiple cloning site (MCS), also known as a polylinker, which is a short nucleic acid sequence that contains many restriction sites. For example, FIG. 1 shows a multiple cloning site, comprising a series of restriction enzyme recognition sites. In certain embodiments, the sequence is inserted in-frame, enabling expression of the inserted sequence. In certain embodiments, after the sequence, such as, e.g., the target protein coding sequence, has been inserted into the cloning site of the vector, a portion of the cloning site remains as flanking sequence on one or both sides of the inserted sequence. In other embodiments, the cloning site no longer remains after the insertion of the sequence into the cloning site of the vector.

As described herein, the nucleic acid sequence encoding (i) the 5' untranslated region and (ii) the adjacent polypeptide tag may be specifically modified to minimize RNA secondary structure both within and/or between these two regions of the mRNA. In certain embodiments, one feature of the method described herein is that RNA optimization is required only in DNA comprising the vector backbone, including the DNA coding for the 5'-UTR and a common N-terminal polypeptide tag, and each gene coding for various target proteins, that is cloned into this vector backbone, need not be optimized individually. Accordingly, nucleic acids within the specific sequence encoding the 5' untranslated region and the adjacent polypeptide tag are replaced with different nucleic acids to minimize RNA secondary structure of the expressed mRNA as described herein. In particular, in certain embodiments, the RNA secondary structure is minimized in the region surrounding the RBS and/or translation initiation site of the expressed mRNA. For example, nucleic acids are replaced to reduce base pairing with the RBS and/or translation initiation site of the expressed mRNA. In certain embodiments, the nucleic acid sequence directly surrounding the RBS site and/or the translation initiation site (e.g., the consensus sequences and sequences between these two sites) is minimally modified or not modified. For example, after modification the RBS site and the translation initiation site remain functionally active. In certain embodiments, nucleotides within the nucleic acid sequence encoding the polypeptide tag are modified in a manner that results in silent mutations.

Prediction of RNA secondary structure can be readily determined by one skilled in the art using techniques and tools known in the art. For example, a skilled artisan may use RNA structure prediction software, including CentroidFold (Hamada et al., 2009), CentroidHomfold (Hamada et al., 2009), CONTRAfold (Do et al., 2006), CyloFold (Bindewald et al.), KineFold (Xayaphoummine et al., 2005; Xayaphoummine et al., 2003), Mfold (Zuker and Stiegler, 1981), GeneBee-NET (Brodskii et al., 1995), (Pknots (Rivas and Eddy, 1999), PknotsRG (Reeder et al., 2007), RNA123 (rna 123.com), RNAfold (Gruber et al., 2008), RNAshapes (Voss et al., 2006), RNAstructure (Mathews et al., 2004), Sfold (Ding et al., 2004), UNAFold (Markham and Zuker, 2008), Crumple (Schroeder et al., 2011), and Sliding Windows & Assembly (Schroeder et al., 2011) among others.

As described herein, a target protein may refer to any of the following non-limiting embodiments: a full-length naturally occurring protein, a polypeptide sequence corresponding to a fragment or domain of a naturally occurring protein sequence, a mutant or modified form of a full-length protein or protein fragment, or a polypeptide sequence coding for a non-natural protein, such as proteins that have been engineered or designed by artificial methods.

Certain embodiments of the invention provide a method of preparing an expression vector, wherein the expression vector comprises, in order of position, a 5' upstream sequence encoding an operable promoter and associated regulatory signals, a sequence encoding the 5' untranslated region of the messenger RNA transcribed from the promoter including a ribosome binding site several nucleotides preceding the translation start codon, a sequence beginning with the start codon encoding a polypeptide tag, and a cloning site that enables "target protein" coding sequences to be inserted into the vector in-frame with the polypeptide tag thus allowing their expression as fusions to the polypeptide tag, wherein the method comprises specifically modifying the entire sequence encoding the 5' untranslated region of the messenger RNA through and including the sequence encoding the polypeptide tag sequence in order to minimize RNA secondary structure upstream of the target insertion site.

In certain embodiments, the method further comprises specifically modifying the second nucleic acid sequence to reduce the presence of rare codons (i.e. mRNA codons for which the corresponding tRNAs are in low abundance in the host cell). For example, rare codons are replaced with high frequency codons to increase expression of any target protein expressed by the vector. Codons that are considered rare are dependent on the selected host cell that is used for expression of the vector and are known to and/or can be readily determined by one skilled in the art. For example, rare codons may be identified using computer software programs known in the art, for example, the Rare Codon Calculator (RaCC) for *E. coli* (nihserver.mbi.ucla.edu/RACC/), jcat.de/, or genomes.urv.es/OPTIMIZER/.

In certain embodiments, the modified region of the nucleic acid sequence spans from the first 5' nucleotide in the expressed mRNA to the last nucleotide of the polypeptide tag.

In certain embodiments, nucleotides within about the last 20 nucleotides of the first nucleic acid sequence are modified (i.e., from the nucleotide that directly precedes the encoded start codon to 20 nucleotides upstream). In certain embodiments, nucleotides within about the last, e.g., 30, 40, 50, 60, 70, 80, 90, 100, 110, 120, 130, 140, 150, 160, 170, 180, 190, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 or 1,000 nucleotides of the first nucleic acid sequence are modified.

In certain embodiments, nucleotides within about the first 20 nucleotides of the second nucleic acid sequence are modified (i.e., from the first nucleotide within the encoded start codon to 20 nucleotides downstream). In certain embodiments, nucleotides within about the first, e.g., 30, 40, 50, 60, 70, 80, 90, 100, 110, 120, 130, 140, 150, 160, 170, 180, 190, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 or 1,000 nucleotides of the second nucleic acid sequence are modified.

In certain embodiments, the expression vector further comprises a target protein coding sequence inserted into the vector in-frame with the nucleic acid tag sequence to encode a fusion protein comprising the polypeptide tag and the target protein.

In certain embodiments, the target protein coding sequence is not modified to minimize RNA secondary structure.

In certain embodiments, the target protein coding sequence is not modified to reduce the presence of rare codons.

In certain embodiments, the target protein coding sequence is modified to minimize RNA secondary structure.

In certain embodiments, the target protein coding sequence is modified to reduce the presence of rare codons.

As used herein, the second nucleic acid sequence encodes at least one polypeptide tag. In certain embodiments, the second nucleic acid sequence encodes more than one polypeptide tag. As used herein, when the second nucleic acid sequence encodes more than one polypeptide tag, the respective sequences that encode each polypeptide tag are joined in-frame to result in a fusion protein that comprises each polypeptide tag. In certain embodiments, the second nucleic acid sequence encodes, e.g., two, three, four, five, etc. polypeptide tags.

As used herein, the second nucleic acid sequence may encode any polypeptide tag appropriate to the particular chosen application or selected target protein (e.g., an affinity purification tag and/or a solubility enhancement tag). Polypeptide tags are known to those skilled in the art. For example, the encoded polypeptide tag may be an Avi-tag, Calmodulin-tag, FLAG-tag, HA-tag, His-tag, Myc-tag, S-tag, SBP-tag, Softag 1, Softag 3, V5 tag, Xpress tag, Isopeptag, Spy tag, BCCP, Glutathione-S-transferase-tag, Green fluorescent protein-tag, Maltose binding protein-tag, Nus-tag, Strep-tag, Thioredoxin-tag, TC tag, Ty tag, Nano-tag, Halo-tag, protein G B1 domain tag, a myxococcus protein S tag or Protein A tag.

Accordingly, in certain embodiments, the at least one encoded polypeptide tag is selected from an Avi-tag, Calmodulin-tag, FLAG-tag, HA-tag, His-tag, Myc-tag, S-tag, SBP-tag, Softag 1, Softag 3, V5 tag, Xpress tag, Isopeptag, Spy tag, BCCP, Glutathione-S-transferase-tag, Green fluorescent protein-tag, Maltose binding protein-tag, Nus-tag, Strep-tag, Thioredoxin-tag, TC tag, Ty tag, Nano-tag, Halo-tag, protein G B1 domain tag, a myxococcus protein S tag or Protein A tag.

In certain embodiments, the second nucleic acid sequence encodes at least one affinity purification tag.

In certain embodiments, the second nucleic acid sequence encodes more than one affinity purification tag.

In certain embodiments, the second nucleic acid sequence encodes two affinity purification tags.

In certain embodiments, the encoded affinity purification tag(s) is/are selected from a Streptavidin binding moiety, a maltose binding protein moiety, and a HIS tag.

In certain embodiments, the Streptavidin binding moiety is a Nano-tag or a biotinylated Avi-tag.

In certain embodiments, the second nucleic acid sequence encodes no affinity purification tags.

In certain embodiments, the second nucleic acid sequence encodes at least one solubility enhancement tag.

In certain embodiments, the second nucleic acid sequence encodes more than one solubility enhancement tag.

In certain embodiments, the second nucleic acid sequence encodes two solubility enhancement tags.

In certain embodiments, the encoded solubility enhancement tag(s) is/are selected from a maltose binding protein tag, a protein G B1 domain tag, and a myxococcus protein S tag.

In certain embodiments, the second nucleic acid sequence encodes no solubility enhancement tags.

In certain embodiments, the second nucleic acid sequence further encodes at least one protease recognition site. In certain embodiments, the second nucleic acid sequence encodes more than one protease recognition site.

As used herein, when the second nucleic acid sequence further encodes a protease recognition site(s), the sequence that encodes this/these site(s) is/are inserted in-frame with the sequence(s) that encode the at least one polypeptide tag to result in a fusion protein that comprises the polypeptide tag(s) and the protease recognition site(s). In certain embodiments, the encoded protease recognition site(s) is/are downstream of the encoded polypeptide tag(s). In certain embodiments, the encoded protease recognition site is/are between a series of encoded polypeptide tag(s).

In certain embodiments, the protease recognition site(s) is/are a Tobacco Etch Virus (TEV), Thrombin, Factor Xa and/or a human rhinovirus (HRV) 3C (e.g., PreScission Protease, GE Healthcare Life Sciences, Pittsburgh, Pa.) protease recognition site.

As described herein, the PreScission Protease is a genetically engineered protein consisting of human rhinovirus 3C protease. It is often produced as a fusion protein with a hexaHis (SEQ ID NO: 5) or GST affinity purification tag. It specifically cleaves between the Gln and Gly residues of the recognition sequence of LeuGluValLeuPheGln/GlyPro (SEQ ID NO: 6).

In certain embodiments, the second nucleic acid sequence is at least about 21 nucleotides in length. In certain embodiments, the second nucleic acid sequence is at least about, e.g., 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 201, 252, 303, 354, 405, 456, 507, 558, 609, 660, 711, 762, 813, 864, 915, 966, or 1,017 nucleotides in length.

In certain embodiments, the target protein coding sequence encodes a transcription factor, a transcription factor domain, an epigenetic regulatory factor, or an epigenetic regulatory factor domain.

In certain embodiments, the target protein coding sequence encodes a polypeptide sequence described in FIG. 9. As described herein, the target protein coding sequence may also encode a polypeptide sequence that has substantial identity to or is a functional equivalent of a polypeptide sequence described in FIG. 9.

In certain embodiments, the target protein coding sequence encodes a protein antigen for producing an affinity capture reagent.

In certain embodiments, the affinity capture reagent is an antibody, an antibody fragment, or an aptamer.

In certain embodiments, the target protein coding sequence encodes a protein antigen for producing an antibody or Fab by phage display.

In certain embodiments, the expression of the target protein is about 1.5 fold greater than the expression of a target protein generated from an expression vector that was not modified as described herein. In certain embodiments, the expression of the target protein is, e.g., about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20, etc., fold greater than the expression of a target protein generated from an expression vector that was not modified as described herein.

As described herein, in certain embodiments, expression of a target protein from a vector that is not TOEET modified as described herein is undetectable, whereas expression of the same target protein from a vector that has been modified as described herein is detectable.

Certain embodiments of the invention provide an expression vector prepared using a method as described herein.

Certain embodiments of the invention provide a target protein expression vector (e.g. a target protein expression vector) comprising, in order of position: a first nucleic acid sequence encoding a 5' untranslated region of an expressed mRNA that comprises a ribosome binding site (RBS); a second nucleic acid sequence encoding a polypeptide tag; and a cloning site, wherein the cloning site enables a target protein coding sequence to be inserted into the vector in-frame with the second nucleic acid sequence to encode a fusion protein comprising the polypeptide tag and the target protein; and wherein the nucleic acid sequence encoding (i) the 5' untranslated region and (ii) the adjacent polypeptide tag has been specifically modified to minimize RNA secondary structure both within and/or between these two regions of the mRNA.

In certain embodiments, the second nucleic acid sequence has been specifically modified to reduce the presence of rare codons.

In certain embodiments, the modified region of the nucleic acid sequence spans from the first 5' nucleotide in the expressed mRNA to the last nucleotide of the polypeptide tag.

In certain embodiments, nucleotides within about the last 20 nucleotides of the first nucleic acid sequence have been modified (i.e., from the nucleotide that directly precedes the encoded start codon to 20 nucleotides upstream). In certain embodiments, nucleotides within about the last, e.g., 30, 40, 50, 60, 70, 80, 90, 100, 110, 120, 130, 140, 150, 160, 170, 180, 190, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 or 1,000 nucleotides of the first nucleic acid sequence have been modified.

In certain embodiments, nucleotides within about the first 20 nucleotides of the second nucleic acid sequence have been modified (i.e., from the first nucleotide within the encoded start codon to 20 nucleotides downstream). In certain embodiments, nucleotides within about the first, e.g., 30, 40, 50, 60, 70, 80, 90, 100, 110, 120, 130, 140, 150, 160, 170, 180, 190, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 or 1,000 nucleotides of the second nucleic acid sequence have been modified.

In certain embodiments, an expression vector as described herein, further comprises a target protein coding sequence inserted into the vector in-frame with the nucleic acid tag sequence to encode a fusion protein comprising the polypeptide tag and the target protein.

In certain embodiments, the target protein coding sequence has not been modified to minimize RNA secondary structure.

In certain embodiments, the target protein coding sequence has not been modified to eliminate rare codons.

In certain embodiments, the target protein coding sequence has been modified to minimize RNA secondary structure.

In certain embodiments, the target protein coding sequence has been modified to eliminate rare codons.

In certain embodiments, the second nucleic acid sequence encodes at least one affinity purification tag.

In certain embodiments, the second nucleic acid sequence encodes more than one polypeptide tag. As used herein, when the second nucleic acid sequence encodes more than one polypeptide tag, the respective sequences that encode each polypeptide tag are joined in-frame to result in a fusion protein that comprises each polypeptide tag. In certain embodiments, the second nucleic acid sequence encodes, e.g., two, three, four, five, etc. polypeptide tags.

As used herein, the second nucleic acid sequence may encode any polypeptide tag appropriate to the particular chosen application or selected target protein (e.g., an affinity purification tag or a solubility enhancement tag). Polypeptide tags are known to those skilled in the art. For example, the encoded polypeptide tag may be an Avi-tag, Calmodulin-tag, FLAG-tag, HA-tag, His-tag, Myc-tag, S-tag, SBP-tag, Softag 1, Softag 3, V5 tag, Xpress tag, Isopeptag, Spy tag, BCCP, Glutathione-S-transferase-tag, Green fluorescent protein-tag, Maltose binding protein-tag, Nus-tag, Strep-tag, Thioredoxin-tag, TC tag, Ty tag, Nano-tag, Halo-tag, protein G B1 domain tag, a myxococcus protein S tag or Protein A tag.

Accordingly, in certain embodiments, the at least one encoded polypeptide tag is selected from an Avi-tag, Calmodulin-tag, FLAG-tag, HA-tag, His-tag, Myc-tag, S-tag, SBP-tag, Softag 1, Softag 3, V5 tag, Xpress tag, Isopeptag, Spy tag, BCCP, Glutathione-S-transferase-tag, Green fluorescent protein-tag, Maltose binding protein-tag, Nus-tag, Strep-tag, Thioredoxin-tag, TC tag, Ty tag, Nano-tag, Halo-tag, protein G B1 domain tag, a myxococcus protein S tag or Protein A tag.

In certain embodiments, the second nucleic acid sequence encodes more than one affinity purification tag.

In certain embodiments, the second nucleic acid sequence encodes two affinity purification tags.

In certain embodiments, the encoded affinity purification tag(s) is/are selected from a Streptavidin binding moiety, a maltose binding protein moiety, and a HIS tag.

In certain embodiments the Streptavidin binding moiety is a Nano-tag or a biotinylated Avi-tag.

In certain embodiments, the second nucleic acid sequence encodes no affinity purification tags.

In certain embodiments, the second nucleic acid sequence encodes at least one solubility enhancement tag.

In certain embodiments, the second nucleic acid sequence encodes more than one solubility enhancement tag.

In certain embodiments, the second nucleic acid sequence encodes two solubility enhancement tags.

In certain embodiments, the encoded solubility enhancement tag(s) is/are selected from a maltose binding protein tag, a protein G B1 domain tag, and a myxococcus protein S tag.

In certain embodiments, the second nucleic acid sequence encodes at least one protease recognition site.

As used herein, when the second nucleic acid sequence further encodes a protease recognition site(s), the sequence that encodes this/these site(s) is/are inserted in-frame with the sequence(s) that encode the at least one polypeptide tag to result in a fusion protein that comprises the polypeptide tag(s) and the protease recognition site(s). In certain embodiments, the encoded protease recognition site(s) is/are downstream of the encoded polypeptide tag(s). In certain embodiments, the encoded protease recognition site is/are between a series of encoded polypeptide tag(s).

In certain embodiments, the protease recognition site(s) is/are a Tobacco Etch Virus (TEV), Thrombin, Factor Xa and/or a HRV 3C protease recognition site.

In certain embodiments, the second nucleic acid sequence is at least about 21 nucleotides in length. In certain embodiments, the second nucleic acid sequence is at least about, e.g., 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 201, 252, 303, 354, 405, 456, 507, 558, 609, 660, 711, 762, 813, 864, 915, 966, or 1,017 nucleotides in length.

In certain embodiments, the target protein coding sequence encodes a transcription factor, a transcription factor domain, an epigenetic regulatory factor, or an epigenetic regulatory factor domain.

In certain embodiments, the target protein coding sequence encodes a polypeptide sequence described in FIG. 9. As described herein, the target protein coding sequence may also encode a polypeptide sequence that has substantial identity to or is a functional equivalent of a polypeptide sequence described in FIG. 9.

In certain embodiments, the target protein coding sequence encodes a protein antigen for producing an affinity capture reagent.

In certain embodiments, the affinity capture reagent is an antibody, an antibody fragment, or an aptamer.

In certain embodiments, the target protein coding sequence encodes a protein antigen for producing an antibody or Fab by phage display.

In certain embodiments, the target protein is expressed at about a 1.5 fold higher level than a target protein generated from an expression vector that was not modified as described herein. In certain embodiments, the target protein is expressed at about, e.g., a 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20, etc., higher level than a target protein generated from an expression vector that was not modified as described herein.

As described herein, in certain embodiments, expression of a target protein from a vector not modified as described herein is undetectable, whereas expression of the same target protein from a vector that has been modified as described herein is detectable.

Certain embodiments of the invention provide a host cell comprising the expression vector as described herein. Host cells are used for the expression of vectors and are known in the art. For example, a host cell may be a bacterial cell, such as *E. coli*.

Certain embodiments of the invention provide a method for expressing a target protein in a host cell, comprising culturing the host cell as described herein for a period of time under conditions permitting expression of the target protein.

In certain embodiments, the target protein is a protein antigen for producing an affinity capture reagent.

In certain embodiments, the affinity capture reagent is an antibody, an antibody fragment, or an aptamer.

In certain embodiments, the target protein is a protein antigen for producing an antibody or Fab by phage display.

In one aspect, the invention features a method of designing an expression vector for expressing a recombinant protein in a host cell, e.g., bacterial cell (such as *E. coli* cell). The method includes steps of: obtaining a first sequence encoding the recombinant protein; obtaining an expression vector containing an insertion site for the first sequence, wherein once inserted at the insertion site, the first sequence is joined in frame with a 5' sequence from the expression vector to form a first fusion sequence that encodes a RNA sequence, the RNA sequence having a Ribosomal Binding Site (RBS) and a translation initiation site; modifying the RNA sequence by (i) designing the RNA sequence so as to minimize RNA secondary structure in a region around the RBS site or translation initiation site, or (ii) optimizing codon usage in the RNA sequence based on codon usage of the host cell, to obtain a second fusion sequence; and cloning the second fusion sequence into the expression vector in such a way to replace the first fusion sequence.

In one embodiment, the designing step or optimizing step is carried out using Transcript-Optimized Expression Enhancement Technology (TOEET) as shown and described herein. In another, the designing step or optimizing step is carried out by introducing a third sequence encoding a N-terminal polypeptide expression-enhancement tag (EET) directly downstream of the initiation site.

The expression-enhancement tag can be an affinity purification tag, such as one having the sequence of an Avi tag, a Nano-tag, or a 6×His tag (SEQ ID NO: 5).

In a second aspect, the invention provides an expression vector that is designed using the method described above. In the expression vector, the second fusion sequence can have a sequence selected from the sequences shown in FIG. 1. In one example, the expression vector is selected from the group consisting of pNESG_Avi6HT and pNESG_Nano6HT. The invention also provides a host cell having the expression vector.

In a third aspect, the invention features a method for increasing the expression and solubility of a recombinant protein in a host cell. The method includes obtaining the just described host cell; culturing the host cell in a culture for period of time; and recovering the recombinant protein from the host cell or the culture. To that end, the recombinant protein can be a protein antigen for producing an affinity capture reagent (such as an antibody, an antibody fragment, or an aptamer) or a protein antigen for producing antibody or Fab by phage display.

In a fourth aspect, the invention provides an immunogenic composition having the recombinant protein produced by the method described above. The composition can be administered to a subject in need thereof for generating an immune response in the subject.

In a fifth aspect, the invention provides a method of generating an antibody (either polyclonal or monoclonal) by, among others, administrating to a subject the immunogenic composition described above.

The invention also provides an isolated polypeptide, a nucleic acid encoding it, a high throughput method for identifying a soluble protein or protein domain, and a high throughput method for isolating a soluble protein or protein domain substantially as shown and described herein.

The term "nucleic acid" refers to deoxyribonucleotides (DNA, e.g., a cDNA or genomic DNA), ribonucleotides (RNA, e.g., an mRNA), or a DNA or RNA analog and polymers thereof, in either single- or double-stranded form, but preferably is double-stranded DNA, made of monomers (nucleotides) containing a sugar, phosphate and a base that is either a purine or pyrimidine. A DNA or RNA analog can be synthesized from nucleotide analogs. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably.

Certain embodiments of the invention encompass isolated or substantially purified nucleic acid compositions. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones, e.g., as these occur in a DNA library such as a cDNA or genomic DNA library. The nucleic acid described above can be used to express a fusion protein of this invention. For this purpose, one can operatively link the nucleic acid to suitable regulatory sequences to generate an expression vector.

The following terms are used to describe the sequence relationships between two or more nucleotide sequences: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)). Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, JMB, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, certain embodiments of the invention provide nucleic acid molecules that are substantially identical to the nucleic acid molecules described herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m 81.5°$ C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In addition to the chemical optimization of stringency conditions, analytical models and algorithms can be applied to hybridization data-sets (e.g. microarray data) to improve stringency.

An expression vector as described herein can be introduced into host cells to produce a fusion protein of this invention. Also within the scope of this invention is a host cell that contains the above-described nucleic acid. Examples include *E. coli* cells, insect cells (e.g., using baculovirus expression vectors), yeast cells, plant cells, or mammalian cells. See e.g., Goeddel, (1990) Gene Expression Technology: Methods in Enzymology 185, Academic Press, San Diego, Calif. To produce a fusion protein of this invention, one can culture a host cell in a medium under conditions permitting expression of the protein encoded by a nucleic acid of this invention, and isolate the protein from the cultured cell or the medium of the cell. The presence of the fusion protein in an occlusion body allows one to prepare the protein from the host cell by simply separating the occlusion body from the host cell. Alternatively, the nucleic acid of this invention can be transcribed and translated in vitro, for example, using T7 promoter regulatory sequences and T7 polymerase.

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation). The peptide, polypeptide, or protein "of this invention" includes recombinantly or synthetically produced fusion versions having the particular domains or portions that are soluble. The term also encompasses polypeptides that have an added amino-terminal methionine (useful for expression in prokaryotic cells).

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide, polypeptide, or protein refers to a peptide, polypeptide, or protein prepared by chemical synthesis. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

Within the scope of this invention are fusion proteins containing one or more of the afore-mentioned sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" peptide, polypeptide, or protein refers to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods.

A functional equivalent of a peptide, polypeptide, or protein of this invention refers to a polypeptide derivative of the peptide, polypeptide, or protein, e.g., a protein having one or more point mutations, insertions, deletions, truncations, a fusion protein, or a combination thereof. It retains substantially the activity of the corresponding unmodified peptide/polypeptide/protein (e.g., the activity of transcription factor). The isolated polypeptide can contain a sequence of a protein as listed in FIG. 8 or 9 or a functional fragment thereof. In general, the functional equivalent is at least 75% (e.g., any number between 75% and 100%, inclusive, e.g., 70%, 80%, 85%, 90%, 95%, and 99%) identical to the corresponding unmodified peptide/polypeptide/protein.

The amino acid composition of the above-mentioned peptide/polypeptide/protein may vary without disrupting their biological activity, e.g., a transcription factor activity, i.e., ability to bind to a DNA element and/or trigger or inhibit the respective cellular response. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in a polypeptide is preferably replaced with another amino acid residue from the same side chain family. Alternatively, mutations can be introduced randomly along all or part of the sequences, such as by saturation mutagenesis, and the resultant mutants can be screened for the respective biological activities.

A polypeptide described in this invention can be obtained as a recombinant polypeptide. To prepare a recombinant polypeptide, a nucleic acid encoding it can be linked to another nucleic acid encoding a fusion partner, e.g., the tags disclosed herein, glutathione-s-transferase (GST), 6×-His epitope tag (or Hexa-His) (SEQ ID NO: 5), 8×-His (or Octa-His) (SEQ ID NO: 7) epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion (e.g., TEV protease digestion), to remove the fusion partner and obtain the recombinant polypeptide of this invention.

The peptide/polypeptide/protein of this invention covers chemically modified versions. Examples of chemically modified peptide/protein include those subjected to conformational change, addition or deletion of a sugar chain, and those to which a compound such as polyethylene glycol has been bound. Once purified and tested by standard methods or according to the methods described in the examples below, the peptide/polypeptide/protein can be included in a composition, e.g., a pharmaceutical composition or an immunogenic composition.

The term "immunogenic" refers to a capability of producing an immune response in a host animal against an antigen or antigens. This immune response forms the basis of the protective immunity elicited by a vaccine against a specific infectious organism. "Immune response" refers to a response elicited in an animal, which may refer to cellular immunity (CMI); humoral immunity or both. "Antigenic agent," "antigen," or "immunogen" means a substance that induces a specific immune response in a host animal. The antigen can be a protein described above, a vector encoding it, a cell having the vector or protein, or any combination thereof.

The term "animal" includes all vertebrate animals including humans. It also includes an individual animal in all stages of development, including embryonic and fetal stages. In particular, the term "vertebrate animal" includes, but not limited to, humans, canines (e.g., dogs), felines (e.g., cats); equines (e.g., horses), bovines (e.g., cattle), porcine (e.g., pigs), as well as in avians. The term "avian" refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary.

The immunogenic composition can be used to generate antibodies against the peptide/polypeptide/protein of this invention. As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, "antibody fragments", may comprise a portion of an intact antibody, generally including the antigen binding or variable region of the intact antibody, the Fab region of the antibody, or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

As used herein, Affinity Capture Reagents are cognate molecules capable or recognizing and binding to a protein antigen, including protein antigens produced by TOEET-optimized expression vectors. Affinity Capture reagents include (but are not limited to) monoclonal and polyclonal antibodies, Fab or Fab fragments generated by phage and related antigen display methods, RNA aptamers, and various protein binding scaffolds which can be used to generate antigen-recognizing molecules.

As used herein, the term "Fc fragment" or "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

A "native sequence Fc region" comprises an amino acid sequence identical to the amino acid sequence of an Fc region found in nature. A "variant Fc region" as appreciated by one of ordinary skill in the art comprises an amino acid sequence which differs from that of a native sequence Fc region by virtue of at least one "amino acid modification." Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and more preferably at least about 90% homology therewith, more preferably at least about 95% homology therewith, even more preferably, at least about 99% homology therewith.

Within the scope of this invention is a composition that contains a suitable carrier and one or more of the agents described above. The composition can be a pharmaceutical composition that contains a pharmaceutically acceptable carrier. The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model.

The composition of this invention can include an adjuvant agent or adjuvant. As used herein, the term "adjuvant agent" or "adjuvant" means a substance added to an immunogenic composition or a vaccine to increase the immunogenic composition or the vaccine's immunogenicity. Examples of an adjuvant include a cholera toxin, *Escherichia* coli heat-labile enterotoxin, liposome, unmethylated DNA (CpG) or any other innate immune-stimulating complex. Various adjuvants that can be used to further increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Pharmaceutical compositions comprising an adjuvant and an antigen may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen.

A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique. For injection, immunogenic or vaccine preparations may be formulated in aqueous solutions, preferably in physiologically compatible buffers such as Hanks's solution, Ringer's solution, phosphate buffered saline, or any other physiological saline buffer. The solution may contain formulatory agents such as suspending, stabilizing and/or dispersing agents. Alternatively, the peptides, polypeptides, or proteins may be in powder form for constitution with a suitable vehicle, e.g., sterile pyrogen-free water, before use.

Determination of an effective amount of the immunogenic or vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the patient, but will typically range from about 0.1 ml to about 5 ml.

This invention also provides methods for making antibodies against the above-described proteins. The antibodies can be either polyclonal or monoclonal.

Polyclonal antibodies against a protein of the invention can be obtained as follows. After verifying that a desired serum antibody level has been reached, blood is withdrawn from the mammal sensitized with the antigen. Serum is isolated from this blood using well-known methods. The serum containing the polyclonal antibody may be used as the polyclonal antibody, or according to needs, the polyclonal antibody-containing fraction may be further isolated from the serum. For instance, a fraction of antibodies that specifically recognize the protein of the invention may be prepared by using an affinity column to which the protein is coupled. Then, the fraction may be further purified by using a Protein A or Protein G column in order to prepare immunoglobulin G or immunoglobulin M.

To obtain monoclonal antibodies, after verifying that the desired serum antibody level has been reached in the mammal sensitized with the above-described antigen, immunocytes are taken from the mammal and used for cell fusion. For this purpose, splenocytes can be preferable immunocytes. As parent cells fused with the above immunocytes, mammalian myeloma cells are preferably used. More preferably, myeloma cells that have acquired the feature, which can be used to distinguish fusion cells by agents, are used as the parent cell.

The cell fusion between the above immunocytes and myeloma cells can be conducted according to known methods, for example, the method of Milstein et al. (Methods Enzymol., 73:3-46, 1981). The hybridoma obtained from cell fusion is selected by culturing the cells in a standard selective culture medium, for example, HAT culture medium (hypoxanthine, aminopterin, thymidine-containing culture medium). The culture in this HAT medium is continued for a period sufficient enough for cells (non-fusion cells) other than the objective hybridoma to perish, usually from a few days to a few weeks. Next, the usual limiting dilution method is carried out, and the hybridoma producing the objective antibody is screened and cloned.

Other than the above method for obtaining hybridomas, by immunizing an animal other than humans with the antigen, a hybridoma producing the objective human antibodies having the activity to bind to proteins can be obtained by the method of sensitizing human lymphocytes, for example, human lymphocytes infected with the EB virus, with proteins, protein-expressing cells, or lysates thereof in vitro, fusing the sensitized lymphocytes with myeloma cells derived from human having a permanent cell division ability.

The obtained monoclonal antibodies can be purified by, for example, ammonium sulfate precipitation, protein A or protein G column, DEAE ion exchange chromatography, an affinity column to which the protein of the present invention is coupled, and so on. The antibody may be useful for the purification or detection of a protein of the invention. It may also be a candidate for an agonist or antagonist of the protein. Furthermore, it is possible to use it for the antibody treatment of diseases in which the protein is implicated. For in vivo administration (in such antibody treatment), human antibodies or humanized antibodies may be favorably used because of their reduced antigenicity.

For example, a human antibody against a protein can be obtained using hybridomas made by fusing myeloma cells with antibody-producing cells obtained by immunizing a transgenic animal comprising a repertoire of human antibody genes with an antigen such as a protein, protein-expressing cells, or a cell lysate thereof. Other than producing antibodies by using hybridoma, antibody-producing immunocytes, such as sensitized lymphocytes that are immortalized by oncogenes, may also be used.

Such monoclonal antibodies can also be obtained as recombinant antibodies produced by using the genetic engineering technique. Recombinant antibodies are produced by cloning the encoding DNA from immunocytes, such as hybridoma or antibody-producing sensitized lymphocytes, incorporating this into a suitable vector, and introducing this vector into a host to produce the antibody. The present invention encompasses such recombinant antibodies as well.

Moreover, the antibody of the present invention may be an antibody fragment or a modified-antibody, so long as it binds to a protein of the invention. For example, Fab, F (ab')$_2$, Fv, or single chain Fv in which the H chain Fv and the L chain Fv are suitably linked by a linker (scFv, Huston et al., Proc. Natl. Acad. Sci. USA, 85:5879-5883, 1988) can be given as antibody fragments. Specifically, antibody fragments are produced by treating antibodies with enzymes, for example, papain, pepsin, and such, or by constructing a gene encoding an antibody fragment, introducing this into an expression vector, and expressing this vector in suitable host cells (for example, Co et al., J. Immunol., 152:2968-2976, 1994; Better et al., Methods Enzymol., 178:476-496, 1989; Pluckthun et al., Methods Enzymol., 178:497-515, 1989; Lamoyi, Methods Enzymol., 121:652-663, 1986; Rousseaux et al., Methods Enzymol., 121:663-669, 1986; Bird et al., Trends Biotechnol., 9:132-137, 1991).

As modified antibodies, antibodies bound to various molecules such as polyethylene glycol (PEG) can be used. The antibody of the present invention encompasses such modified antibodies as well. To obtain such a modified antibody, chemical modifications are done to the obtained antibody. These methods are already established in the field.

The antibody of the invention may be obtained as a chimeric antibody, comprising non-human antibody-derived variable region and human antibody-derived constant region, or as a humanized antibody comprising non-human antibody-derived complementarity determining region (CDR), human antibody-derived framework region (FR), and human antibody-derived constant region by using conventional methods.

Antibodies thus obtained can be purified to uniformity. The separation and purification methods used in the present invention for separating and purifying the antibody may be any method usually used for proteins. For instance, column chromatography, such as affinity chromatography, filter, ultrafiltration, salt precipitation, dialysis, SDS-polyacrylamide gel electrophoresis, isoelectric point electrophoresis, and so on, may be appropriately selected and combined to isolate and purify the antibodies (Antibodies: a laboratory manual. Ed Harlow and David Lane, Cold Spring Harbor Laboratory, 1988), but is not limited thereto. Antibody concentration of the above mentioned antibody can be assayed by measuring the absorbance, or by the enzyme-linked immunosorbent assay (ELISA), etc. Protein A or Protein G column can be used for the affinity chromatography. Protein A column may be, for example, Hyper D, POROS, Sepharose F.F., and so on.

Other chromatography may also be used, such as ion exchange chromatography, hydrophobic chromatography, gel filtration, reverse phase chromatography, and adsorption chromatography (Strategies for Protein Purification and Characterization: A laboratory Course Manual. Ed. by Marshak D. R. et al., Cold Spring Harbor Laboratory Press, 1996). These may be performed on liquid chromatography such as HPLC or FPLC.

Examples of methods that assay the antigen-binding activity of the antibodies of the invention include, for example, measurement of absorbance, enzyme-linked immunosorbent assay (ELISA), enzyme immunoassay (EIA), radio immunoassay (RIA), or fluorescent antibody method. For example, when using ELISA, a protein of the invention is added to a plate coated with the antibodies of the invention, and next, the objective antibody sample, for example, culture supernatants of antibody-producing cells, or purified antibodies are added. Then, secondary antibody recognizing the antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore may be used.

The following non-limiting examples set forth herein below illustrate certain aspects of the invention.

EXAMPLE 1

This example describes two specific EET tags designed utilizing TOEET. These EETs were engineered and subcloned into the pET15_NESG expression vector (Acton et al., 2011). They contain dual tandem protein purification tags and a protease cleavage site to facilitate purification of the resulting proteins. These include the 6×-His tag (SEQ ID NO: 5) (Crowe et al., 1994), and one of two Streptavidin binding moieties, either the Avi-tag (Scholle et al., 2004) or the Nano-tag (Lamla and Erdmann, 2004). The Nano-tag binds directly to streptavidin (Lamla and Erdmann, 2004); the Avi-tag is a substrate for the enzyme BirA which can be used to catalyze the covalent attachment of biotin to the Avi Tag (Scholle et al., 2004). These tandem tags allow for two separate affinity purification steps, (i) Ni-based immobilized metal affinity chromatography (IMAC) and (ii) high-affinity Streptavidin-based chromatography. This dual purification strategy allows preparation of highly purified proteins using high-throughput affinity purification methods. The Tobacco Etch Virus (TEV) protease recognition site (Kapust et al., 2002) engineered into these EETs allows removal of the affinity tags, if required, after expression and purification of the protein target.

Briefly, in designing the DNA sequences coding for these EETs, the coding sequence of one of the two Streptavidin binding moieties i.e., Avi-tag (SEQ ID NO:1 —MSGLNDIFEAQKIEWHE) or Nano-tag (SEQ ID NO:2—MDVEAWLDERVPLVET) (Lamla and Erdmann, 2004; Scholle et al., 2004), a 6×-His tag (SEQ ID NO: 5) (Crowe et al., 1994), and a TEV protease recognition site (Kapust et al., 2002) were fused in frame and optimized to have a high Codon Adaptation Index (Sharp and Li, 1987) (FIG. 1). The DNA sequence coding for the EET was optimized with TOEET, together with the 5'-untranslated region of the pET15-NESG expression vector, to generate the expression vectors pNESG_Avi6HT and pNESG_Nano6HT, shown in FIG. 1. These features functioned together to enhance translation initiation and protein expression levels.

Using these expression vectors (FIG. 1), protein expression resulted in T7 RNA Polymerase mediated transcription producing an mRNA transcript consisting of (i) vector sequence (pET15_NESG-5'- untranslated region), (ii) nucleotides coding for the EET, and (iii) nucleotides coding for the target protein sequence. Both the untranslated region of the vector upstream of the EET-coding region, and the RNA coding for the EET itself were optimized to avoid secondary structure formation within and between these regions of the mRNA transcript. In this particular implementation, the length of the optimized nucleotide sequence coding for the EET was about 90 nucleotides. Together with the 70 upstream 5'-untranslated nucleotides of the transcript driven by the T7 promoter of the vector, the 5'-region of the transcript was optimized as a unit of about 160 nucleotides. Longer optimized nucleotide sequences, and potentially somewhat shorter optimized nucleotide sequences may also be effective in creating TOEET-based expression-enhanced vectors.

Figure 2:
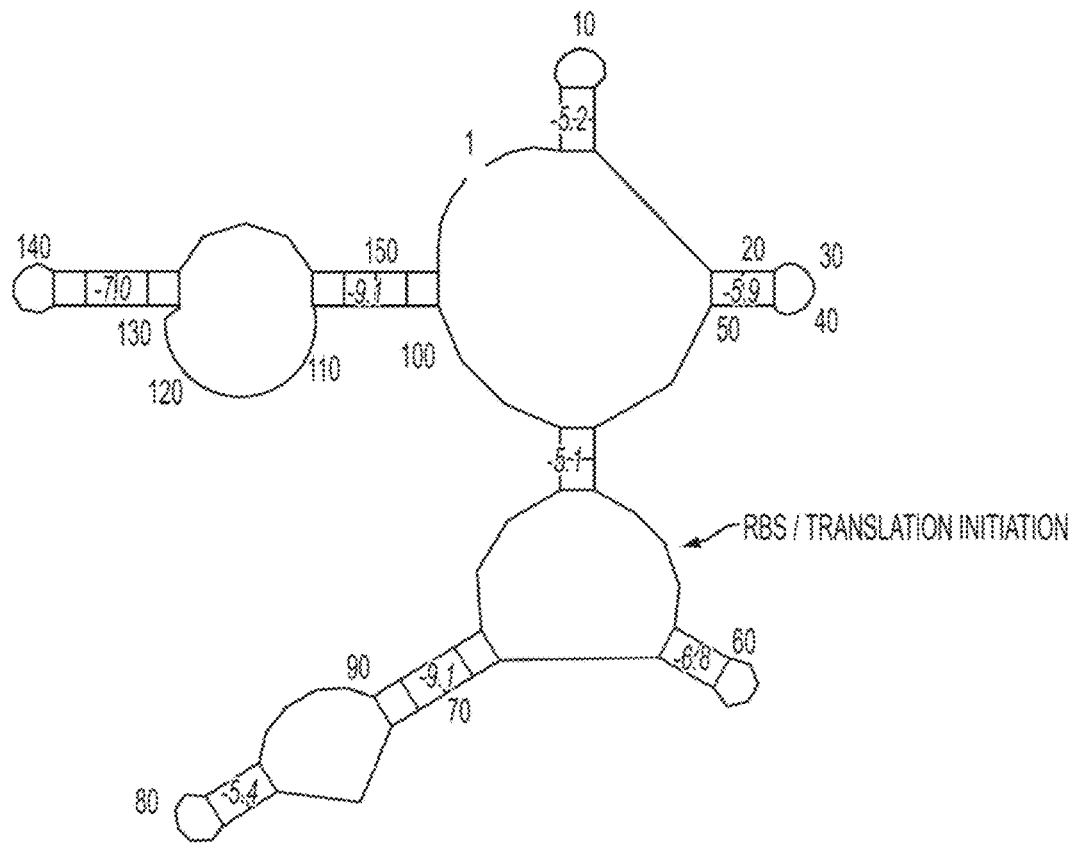
FIG. 2 is a diagram showing the predicted mRNA secondary structure resulting from T7-RNA Polymerase based transcription off of the pNESG_Avi6HT T7 promoter. Numbering of the transcript from nucleotides 1-156 is indicated; negative numbers (in italics) show the estimated strength, in kcal/mole, of the predicted base-paired regions. The arrow indicates a predicted open structure (lack of base pairing) at the RBS/translation initiation region. RNA secondary structure predictions were done using GeneBee-NET (genebee.msu.su/services/rna2_reduced.html).

The optimized regions of the pNESG_Avi6HT and pNESG_$_{Nano}$6HT based TOEET vectors are shown in FIG. 1. The figure shows the DNA sequences, RNA sequences, and the translated protein tag (SEQ ID NO:3—MSGLNDIFEAQKIEWHEHHHITHHENLYFQSH and SEQ ID NO:4—MDVEAWLDERVPLVETHHHHHHENLYFQSH, respectively) sequences of the expression vectors, along with the DNA sequence coding for the multiple cloning site (MCS), a series of restriction endonuclease sites used for cloning into the expression plasmids. FIG. 2 shows, as an example, the predicted RNA secondary structure in transcripts generated from the pNESG_Avi6HT vector, highlighting the lack of predicted RNA secondary structure near the RBS/translation initiation site.

Figure 4:
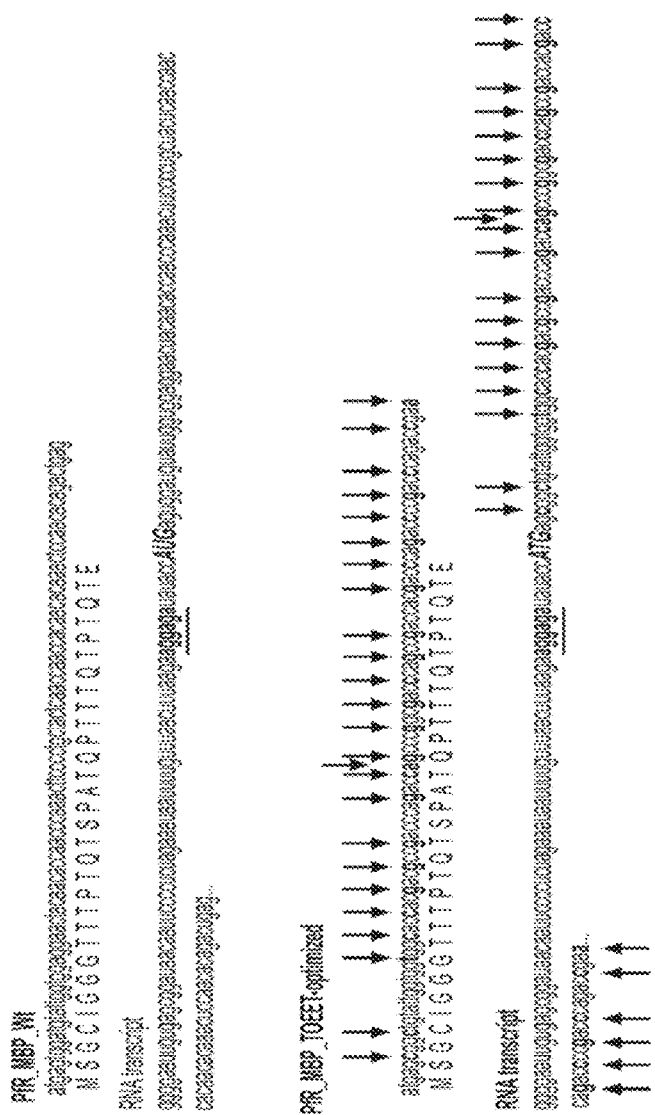
FIG. 4. Wild-Type and TOEET-Optimized *Pyrococcus furiosus* (PfR) Maltose Binding Protein (MBP). The sequences at the top corresponds to the first 30 residues of the wild-type PfR-MBP DNA sequence lacking the native secretion signal. The protein open reading frame (DNA sequence) is shown above the corresponding protein sequence. Directly below is the T7 RNA polymerase mediated RNA transcript resulting from the cloning of the PfR-MBP into the pET15_NESG backbone. The Ribosome Binding Site (RBS) is underlined and highlighted in bold, the translation initiation codon is shown in bold-italics. The lower set of sequences correspond to TOEET-optimized PfR-MBP. Bold nucleotides with arrows indicate positions where silent mutations were introduced for codon optimization, predicted decrease in RNA secondary structure in the regions of the RBS and translation initiation codon, or both. The RNA transcript for the TOEET optimized sequence is also shown following the parameters outlined above. The silent mutations were introduced using primers incorporating the nucleotide changes and 5 successive rounds of PCR, negating the need for expensive total gene synthesis. Figure discloses SEQ ID NOS 14-19, respectively, in order of appearance.

A third vector comprising the *Pyrococcus furiosus* (PfR) Maltose Binding Protein (MBP) was also constructed and optimized using TOEET. The MBP from *Pyrococcus furiosus* is much more thermally stable than that of *E coli*, and is expected to provide a more robust solubilization enhancement tag and affinity purification tag. Proteins that are expressed but not soluble in cell extracts can be solubilized and used successfully as antigens using various methods of solublization, including urea and guanidine denaturtants (Agaton et al, 2003). The PfR MBP provides improved purification of target proteins under such partially denaturing conditions or other harsh conditions. The sequences shown at the top of FIG. 4 correspond to the first 30 residues of the wild-type PfR-MBP DNA sequence lacking the native secretion signal. The protein open reading frame (DNA sequence) is shown above the corresponding protein sequence and directly below is the T7 RNA polymerase mediated RNA transcript resulting from the cloning of the PfR-MBP into the pET15_NESG backbone. The lower set of sequences shown in FIG. 4 correspond to TOEET optimized PfR-MBP. Silent mutations were introduced for codon optimization or to decrease the predicted RNA secondary structure in the regions of the RBS and translation initiation codon, or both. The silent mutations were introduced using primers incorporating the nucleotide changes and 5 successive rounds of PCR, negating the need for expensive total gene synthesis.

Figure 5:
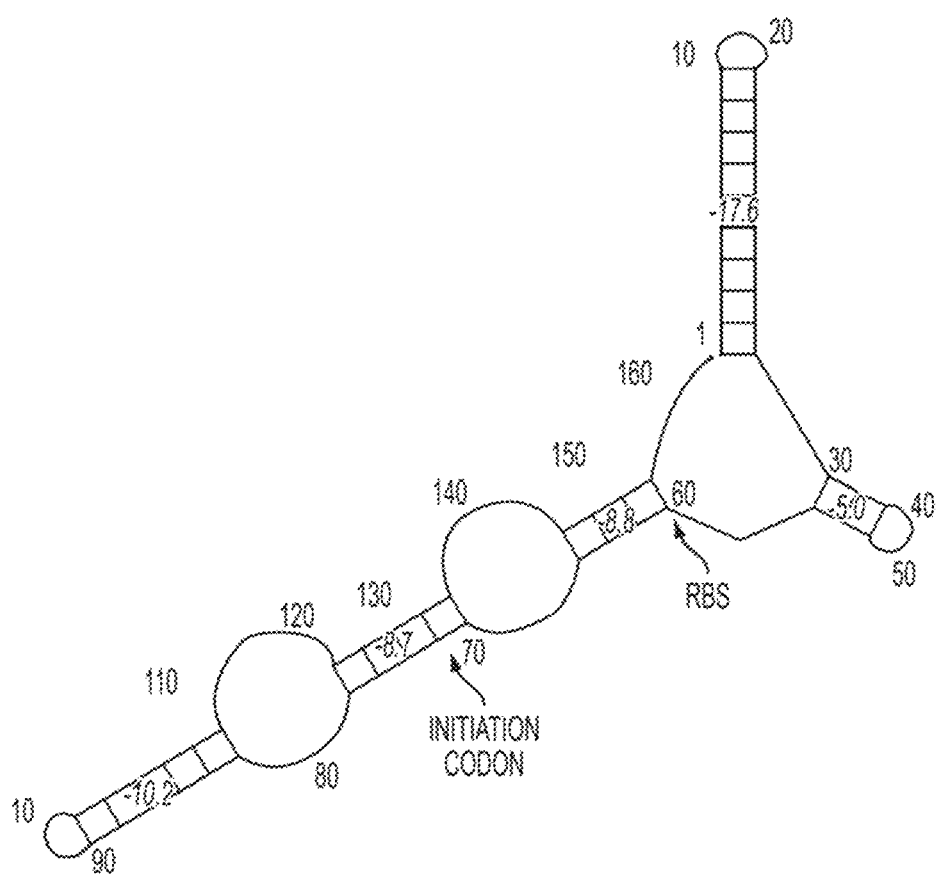
FIG. 5. The predicted mRNA secondary structure resulting from T7-RNA Polymerase based transcription off of the pET15_NESG vector backbone with *Pyrococcus furiosus* (PfR) Maltose Binding Protein (MBP) without TOEET optimization. The arrows indicate significant secondary structure (base pairing) at both the Ribosome Binding Site (RBS) and the translation initiation site (Initiation Codon). RNA secondary structure predictions were performed using GeneBee-NET (genebee.msu.su/services/rna2_reduced.html).
Figure 6:
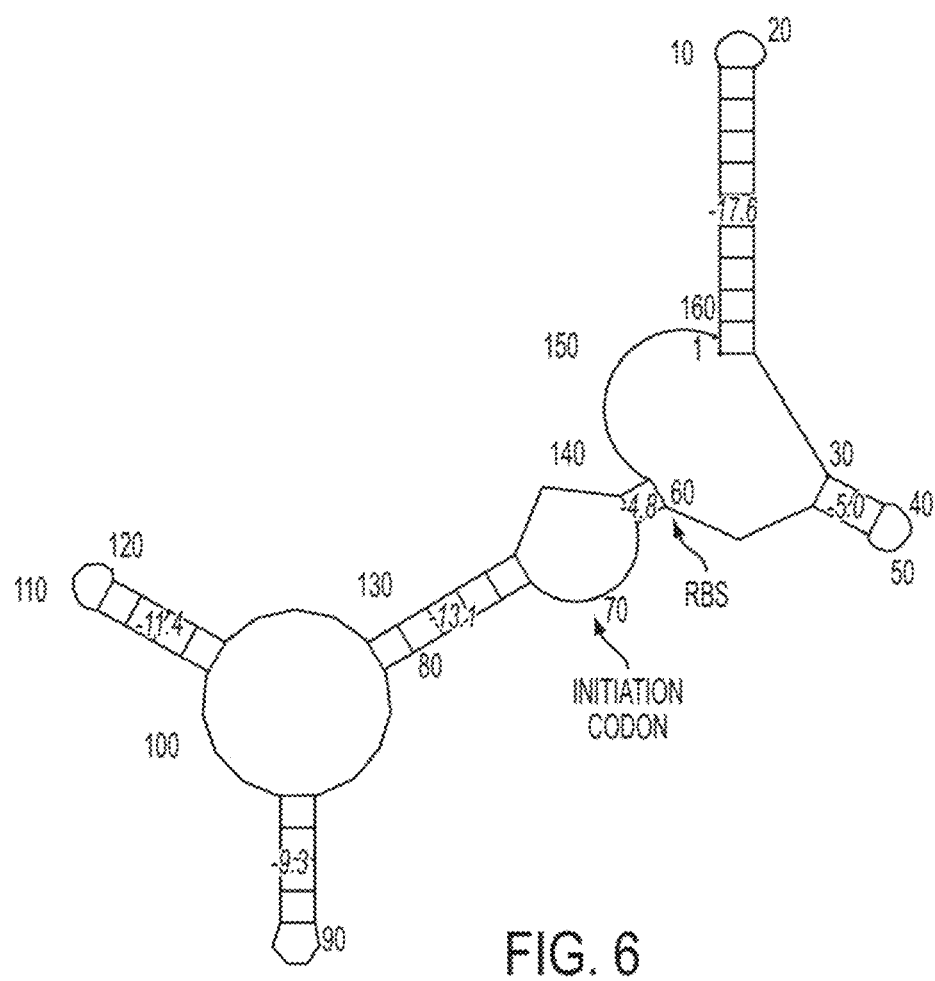
FIG. 6. The predicted mRNA secondary structure resulting from T7-RNA Polymerase based transcription off of the pET15_NESG vector backbone with *Pyrococcus furiosus* (PfR) Maltose Binding Protein (MBP) after TOEET optimization. The arrows indicates the Ribosome Binding Site (RBS) and the translation initiation site (Initiation Codon) and the prediction of significantly greater open structure (lack of base pairing) after TOEET optimization. RNA secondary structure predictions were done using GeneBee-NET (genebee.msu.su/services/rna2_reduced.html).

The predicted mRNA secondary structure resulting from T7-RNA Polymerase based transcription off of the pET15_NESG vector backbone with *Pyrococcus furiosus* (PfR) Maltose Binding Protein (MBP) without TOEET optimization is shown in FIG. 5. Significant secondary structure (base pairing) at both the Ribosome Binding Site (RBS) and the translation initiation site (Initiation Codon) is predicted. The predicted mRNA secondary structure resulting from T7-RNA Polymerase based transcription off of the pET15_NESG vector backbone with *Pyrococcus furiosus* (PfR) Maltose Binding Protein (MBP) after TOEET optimization is shown in FIG. 6. As illustrated by FIG. 6, significantly greater open structure (lack of base pairing) after TOEET optimization is predicted.

EXAMPLE 2

The results obtained from expression studies with the above-described new vectors demonstrated that the TOEET strategy is both extremely successful and robust. In this example, similar expression and solubility studies were carried out using a high throughput methodology for the identification and isolation of soluble proteins and protein domains.

As mentioned above, the isolation of soluble, well-folded proteins and protein domains is of great use and importance to the biotechnology industry and biological researchers as a whole. However, the production of such protein reagents remains extremely challenging, especially in the cost effective, commonly used bacterial expression systems. These *Escherichia coli* expression systems are often successful in the production of simple bacterial proteins but are far less amenable to the production of eukaryotic, mulitdomain proteins or protein complexes, often resulting in no or low levels of expression and/or solubility (greatly complicating or thwarting their production as a protein reagent). There are a variety of reasons that contribute to the lower success rate of these proteins in bacterial expression systems including the fact that eukaryotic proteins are frequently multidomain in nature, this often results in misfolding when expressed using simple prokaryotic expression systems (Netzer and Hartl, 1997). Another major reason for the higher attrition rate relates to the increased levels of disordered regions in human and other eukaryotic proteins in comparison to simpler organisms (Lui et al., 2002). These disordered regions likely cause aggregation and misfolding in *E. coli* expression systems leading to proteins or domains with low expression and/or solubility, again, greatly interfering with their production.

To circumvent these issues, the NESG Construct Optimization Software and High ThroughPut (HTP) Molecular Cloning and Expression Screening Platform and Automated Purification Pipeline methods were developed for assaying multiple alternative constructs to identify soluble proteins or domains (Methods in Enzymology, Vol. 493, Burlington: Academic Press, 20~11, pp. 21-60.). Briefly, the NESG Construct Optimization Software used reports from the from the DisMeta Server (nmr.cabm.rutgers.edu/bioinformatics/disorder), a metaserver that generated a consensus analysis of eight sequence-based disorder predictors to identify protein regions that are likely to be disordered. In addition, secondary structure, transmembrane and signal peptides among others were also predicted. This data along with multiple sequence alignments of homologous proteins were used to predict possible structural domain boundaries. Based on this information, the NESG Construct Optimization software generated nested sets of alternative constructs, for full-length proteins, multidomain constructs, and single domain constructs. Primers for cloning were then designed using the software Primer Primer (Everett, J.K.; Acton, T.B.; Montelione, G.T.J. Struct. Funct. Genomics 2004, 5: 13-21. Primer Prim'r: A web based server for automated primer design.). Thus for a single targeted region, multiple open reading frames were generally designed varying the N and/or C-terminal sequences. These alternative constructs often possessed significantly better expression, solubility and biophysical behavior than their full-length parent sequences, increasing the possibility of successfully producing a protein reagent.

Although the NESG Construct Optimization Software identified protein subsequences that were more likely to produce soluble well-behaved samples, several variants of each were assayed to identify constructs amenable to protein sample production. Therefore the high-throughput NESG Molecular Cloning and Expression Screening Platform was developed utilizing 96-well parallel cloning/E. coli expression and Qiagen BioRobotS000-based liquid handling. Briefly, protein target sequences (constructs) were PCR amplified from Reverse Transcriptase (RT) generated cDNA pools or genomic DNA, gel purified and extracted in 96-well format (robotic liquid handling) and subcloned into pET_NESG, a series of T7 based (Novagen) bacterial expression vectors generated at Rutgers, using InFusion (Clonetech) Ligation Independent Cloning (LIC). The RT generated cDNA pools were derived from normal and disease tissue (tumor cells and cell lines) allowing for the isolation of wild-type and polymorphic proteins. Correct clones (containing the desired protein open reading frame) were identified using plate based-PCR assays. An automated DNA Miniprep Protocol isolated the nascent expression vectors and a 96-well transformation protocol was used to introduce the plasmids into the BI21(DE3) pMgK E. coli expression strain. Following overnight growth, a single representative colony from each well (96) was transferred to LB in a 96-well S-Block and incubated for 6 hours. Automated liquid handling was then utilized to produce a 500 microliter overnight subculture of each of the 96 constructs in a single 96-well S-block. An aliquot of each well was then subcultured into the corresponding well of one of four 24-well blocks containing 2 ml of fresh media and incubated at 37° C. until mid-log phase growth. Protein expression is induced with IPTG (Isopropyl13-D-1-thiogalactopyranoside) and incubated overnight at 17° C. The cells were harvested using automated liquid handling and sonicated in 96-well format. The expression and solubility of each construct was visualized by SDS-PAGE analysis and constructs suitable for protein production were identified.

The soluble expression constructs were then fermented in large volume using parallel fermentation system, consisting of 2.5-L baffled Ultra Yield™ Fernbach flasks, low-cost platform shakers, controlled temperature rooms and specialized MJ9 media (Jansson et al. 1996). This generally produced 10-100 mg of protein per liter of culture. The resulting proteins were then purified using high-throughput AKTAxpress-based parallel protein purification system. This consisted of a two-step automated Ni-affinity purification (pET_NESG imparts a 6×-His tag (SEQ ID NO: 5)) followed by gel filtration chromatography. The purified proteins were then analyzed for quality including molecular weight validation by MALDI-TOF mass spectrometry, homogeneity analysis by SDS-PAGE, aggregation screening by analytical gel filtration with static light scattering, and finally concentration determination was performed.

Together the NESG Construct Optimization Software, Molecular Cloning and Expression Screening Platform and Automated Purification Pipeline allow for identification and isolation of large numbers of soluble well-behaved protein reagents in a time efficient and cost effective manner. Without this technology, many of the proteins would prove elusive in regard to production as a protein reagent.

In this process, target protein expression constructs were designed using proprietary bioinformatics methods, cloning was done using robotic methods and protocols, and Expression (E, ranging from 0 to 5) and Solubility (S, ranging from 0 to 5) screening were performed in a high throughput fashion and assessed using SDS-PAGE analysis. The read out (ES score=E score×S score, ranging from 0 to 25) provided a measure of the usability of a particular target construct and expression vector system combination for large-scale protein sample production. In general, constructs providing ES scores≥9 in this high throughout expression and solubility assay provided milligram-per-liter (or tens-of-milligram per liter) quantities of protein samples in medium scale (0.5-3 L) shake flask fermentations.

As a demonstration of the TOEET technology, a set of approximately 96 human transcription factor genes and epigenetic regulatory factor genes were cloned into the pET15_NESG vector (Acton et al., 2011) lacking a TOEET sequence, and into both the pNESG_Avi6HT and pNESG_Nano6HT vectors. These expression vectors were constructed, and the expression and solubility of target proteins assessed, using the technology outlined above. The results of this study are summarized in FIG. 8.

Figure 3:
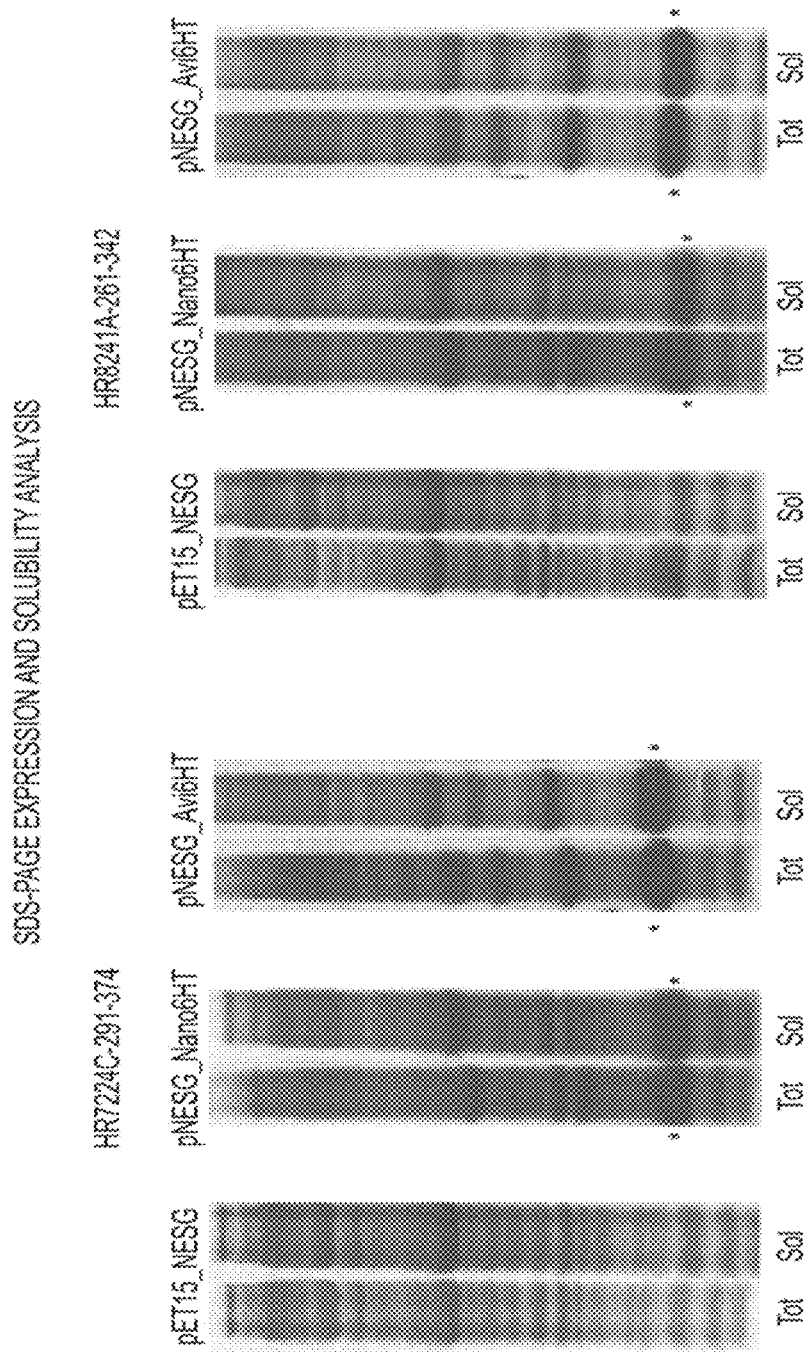
FIG. 3 is a set of photographs showing representative SDS-PAGE analysis of expression and solubility for two human protein domains cloned into each of the three vectors pET15_NESG, pNESG_Nano6HT and pNESG_Avi6HT. Left Panel shows the expression and solubility of HR7724C (HUGO ID: ZNF281) residues 291-374. Right Panel shows the expression and solubility of HR8241 (HUGO ID: NR4A21) residues 261-342. Total cell lysate (Tot) and the soluble portion (Sol) of the cell lysate are run in adjacent lanes for each of the two protein domains and the three expression vectors. An asterisk (*) indicates an overexpressed band of the correct size. Note the lack of protein expression in the case of pET15_NESG constructs.

It was found that, using the pET15_NESG vector, only 20 of 99 constructs provided expression and solubility levels that can support scale-up protein sample production (ES score≥9; boxed numbers in FIG. 8). In contrast, using the pNESG_Nano6HT or pNESG_Avi6HT on this same set of target genes provided a significant increase in the number of highly-expressed and soluble targets suitable for scale-up production. As shown in FIG. 8, 42 of 98 tested, and 34 of 94 tested protein targets exhibited an ES score≥9 (boxed numbers in FIG. 8) in the pNESG_Avi6HT and pNESG_Nano6HT vectors, respectively. Several SDS-PAGE gels illustrating these expression and solubility enhancements are shown in FIG. 3. Not only were more of these 99 human protein target genes expressed using TOEET, but both expression levels and solubility were generally increased. For example, while about half of the 99 protein targets had expression value E=0 (i.e. no detectable expression) in the pET15_NESG vector (lacking TOEET), 95 of the 99protein targets had expression values E≥2 in either the pNESG_Nano6HT and pNESG_Avi6HT vectors (FIG. 8); many have E values E=5 (the maximum level typically observed) in the expression vectors using TOEET.

Construct designs for a larger set of more than 2,000 human transcription factor proteins and domains are listed in FIG. 9. A large number of the proteins listed in FIG. 9 have been cloned into vectors optimized by TOEET, such as the pNESG_Nano6HT and pNESG_Avi6HT vectors, and exhibit high levels expression and solubility. Analysis of these data indicates that both the pNESG_Nano6HT vector and pNESG_Avi6HT vectors produced greater expression and solubility levels than a standard pET15_NESG vector that has not been optimized using the TOETT technology described in this disclosure.

Overall, TOEET allows for the production of a significantly greater number of human proteins and protein domains. The higher ES values obtained using TOETT also allow for simpler production and purification of the target proteins, since high ES scores mean that the cell extract has a larger amount of the target protein relative to background proteins.

The pNESG_Avi6HT also allows for the production of protein samples that can be readily biotinylated in the EET tag sequence. The pNESG_Nano6HT tag also provides a means for simple production of a streptavidin-binding protein (Scholle et al., 2004). Such biotinylated or Nano-tagged protein samples can be used for a variety of processes, including phage display antibody production, as well as for screening and discovering protein-protein and protein-nucleic acid interactions.

EXAMPLE 3

Figure 7A:
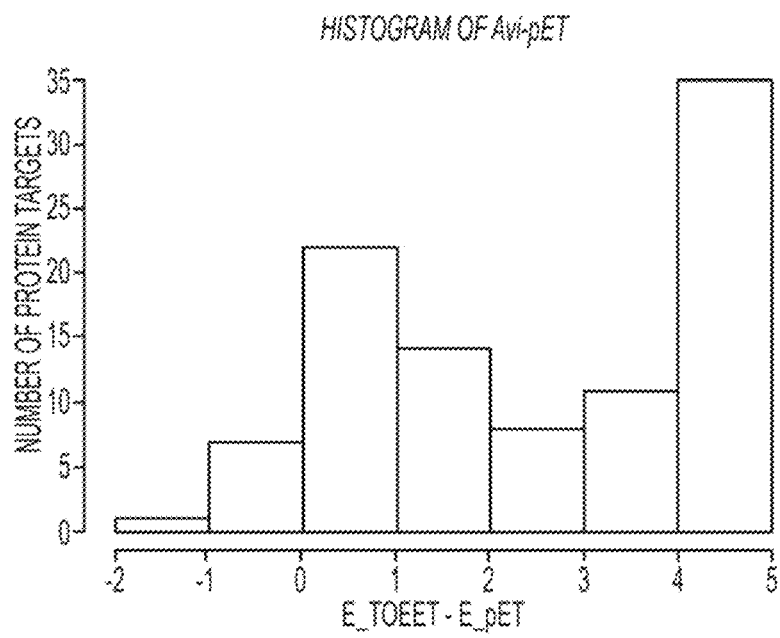
FIGS. 7*a-b*. Histogram plots comparing Expression scores (E ranging from 0 to 5) using the TOEET technology (E_TOEET) compared to expression scores for the same target protein using a pET vector lacking TOEET technology (E_pET). The data shown in FIG. 7*a* is for 98 protein target genes cloned into the pNESG_Avi6HT TOEET vector compared with the exact same genes cloned into the pET15_NESG vector (lacking TOEET). The data shown in FIG. 7*b* is for 94 protein target genes cloned into the pNESG_Nano6HT TOEET vector compared with the exact same genes cloned into pET15_NESG vector (lacking TOEET). In these histogram plots, a value E_TOEET−E_pET=0 indicates that the expression levels for both vectors were identical; values E_TOEET−E_pET>0 indicate that the TOEET technology provided higher level expression, values E_TOEET−E_pET<0 indicate that the TOEET technology provided lower level expression.
Figure 7B:
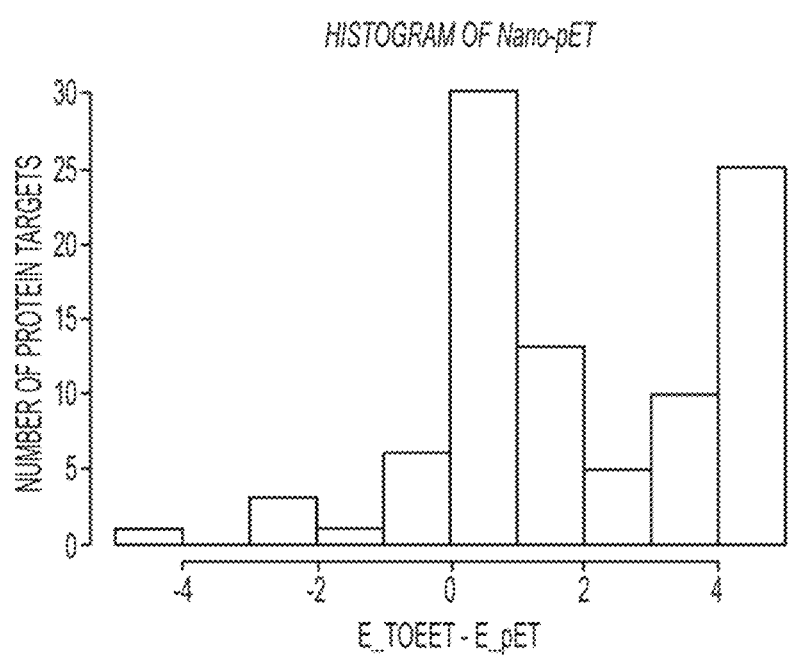

In certain applications, proteins that are expressed but not soluble in cell extracts can be solubilized and used successfully as antigens using various methods of solubilization, including urea and guanidine denaturants (Agaton et al. 2003). Accordingly, the ability to express a protein target, even it is not soluble in the high throughput Expression-Solubility screen described above [NESG High ThroughPut (HTP) Molecular Cloning and Expression Screening Platform methods] is critical, since if the protein cannot be expressed at all it is not possible to generate a suitable antigen. Accordingly, a particularly important value of the TOEET technology is enhancement of protein expression (E), regardless of the resulting solubility. To illustrate this point, histogram plots are presented in FIGS. 7a and 7b comparing Expression scores (E ranging from 0 to 5) using the TOEET technology (E_TOEET) compared to expression scores for the same target protein using a pET vector lacking TOEET technology (E_pET). The data shown in FIG. 7a is for 98 protein target genes cloned into the pNESG_Avi6HT TOEET vector compared with the exact same genes cloned into the pET15_NESG vector (lacking TOEET). The data shown in FIG. 7b is for 94 protein target genes cloned pNESG_Nano6HT TOEET vectors compared with the exact same genes cloned into pET15_NESG vector (lacking TOEET). In these histogram plots, a value E_TOEET−E_pET=0 indicates that the expression levels for both vectors were identical; values E_TOEET−E_pET>0 indicate that the TOEET technology provided higher level expression, values E_TOEET−E_pET<0 indicate that the TOEET technology provided lower level expression. For both target sets, the vast majority of genes exhibit much higher expression in the pNESG_Avi6HT TOEET and pNESG_Nano6HT TOEET vectors compared with the pET15_NESG vector (lacking TOEET). In many cases, E_TOEET−E_pET is 4 or 5, indicating that the expression in the non-TOEET vector was 0 or 1, which is too low to be useful for antigen production. Thus the TOEET vectors often provide high level expression of proteins which cannot be expressed at all, or those with are otherwise expressed as such marginal levels as to be useless for antigen production.

EXAMPLE 4

A representative method for practicing certain embodiments of the invention is described below.

The first step in the method is to identify the residues of the chosen tag/protein and the corresponding DNA sequences to be modified, for example, the $1^{st}$ 30 residues of the tag/protein. Low usage codons are identified and are changed to optimal codons either manually or using servers, for example, such as jcat.de/ or genomes.urv.es/OPTIMIZER/, among others (Step 2). The transcription start site of vector and the resulting 5' untranslated region is then identified (Step 3). The 5' UTR RNA sequence is fused in silico with the optimized RNA sequence encoding the tag/protein (e.g., the first 30 residues of the tag/protein) (Step 4). Various RNA secondary structure prediction methods may then be used to analyze the fused sequence, such as, for example: genebee.msu.su/services/rna2_reduced.html, rna.tbi.univie.ac.at/cgi-bin/RNAfold.cgi (Maximum Free Energy with partition function) or ncrna.org/centroidfold/ (Centroid Estimators-Statistical Decision Theory) (Step 5). The RBS and Initiation codon (IC) are then identified in the secondary structure prediction and the RNA positions in the first, e.g., 30 residues of the tag/protein that pair to the RBS/IC regions are determined (Step 6). Subsequently, alternative high frequency codons for the given residues base pairing with the RBS/IC are substituted and secondary structure is recalculated (Step 7). Steps 5 through 7 may be repeated until the secondary structure in RBS/IC is minimized and there is general agreement with the between the prediction servers (e.g., multiple predication servers may be used, such as the three servers listed above). This information is then used to design and produce the TOEET-optimized expression vector. Target proteins may then be cloned and expressed into the resulting expression system using the NESG Construct Optimization Software and High Throughput (HTP) Molecular Cloning and Expression Screening Platform and Automated Purification Pipeline methods, as outlined above.

REFERENCES

Acton, T. B., et al., 2011. Preparation of protein samples for NMR structure, function, and small-molecule screening studies. Methods Enzymol. 493, 21-60.

Agaton et al., Molecular & Cellular Proteomics 2:405-414, 2003.

Bindewald, E., et al., CyloFold: secondary structure prediction including pseudoknots. Nucleic Acids Res. 38, W368-72.

Brodskii, L. I., et al., 1995. [GeneBee-NET: An Internet based server for biopolymer structure analysis]. Biokhimiia. 60, 1221-30.

Crowe, J., et al., 1994. 6xHis-Ni-NTA chromatography as a superior technique in recombinant protein expression/purification. Methods Mol Biol. 31, 371-87. "6xHis" disclosed as SEQ ID NO: 5.

Ding, Y., et al., 2004. Sfold web server for statistical folding and rational design of nucleic acids. Nucleic Acids Res. 32, W135-41.

Do, C. B., et al., 2006. CONTRAfold: RNA secondary structure prediction without physics-based models. Bioinformatics. 22, e90-8.

Gonzalez de Valdivia, E. I., Isaksson, L. A., 2004. A codon window in mRNA downstream of the initiation codon where NGG codons give strongly reduced gene expression in Escherichia coli. Nucleic Acids Res. 32, 5198-205.

Gruber, A. R., et al., 2008. The Vienna RNA websuite. Nucleic Acids Res. 36, W70-4.

Hamada, M., et al., 2009. Predictions of RNA secondary structure by combining homologous sequence information. Bioinformatics. 25, i330-8.

Jansson, M.; et al., 1996. High-level production of uniformly $^{15}$N- and $^{13}$C-enriched fusion proteins in *Escherichia coli*. B. J. Biomol. NMR. 7, 131-141

Kapust, R. B., et al., 2002. The P1' specificity of tobacco etch virus protease. Biochem Biophys Res Commun. 294, 949-55.

Kudla, G., et al., 2009. Coding-sequence determinants of gene expression in *Escherichia coli*. Science. 324, 255-8.

Lamla, T., Erdmann, V. A., 2004. The Nano-tag, a streptavidin-binding peptide for the purification and detection of recombinant proteins. Protein Expr Purif. 33, 39-47.

Lui et al., 2002, Loopy proteins appear conserved in evolution. J Mol Biol. 322-53-64)

Markham, N. R., Zuker, M., 2008. UNAFold: software for nucleic acid folding and hybridization. Methods Mol Biol. 453, 3-31.

Mathews, D. H., et al., 2004. Incorporating chemical modification constraints into a dynamic programming algorithm for prediction of RNA secondary structure. Proc Natl Acad Sci USA. 101, 7287-92.

Netzer and Hartl, 1997. Recombination of protein domains facilitated by co-translational folding in eukaryotes. Nature. 358-343-9.

Nomura, M., et al., 1984. Influence of messenger RNA secondary structure on translation efficiency. Nucleic Acids Symp Ser. 173-6.

Quan, J., et al., 2011. Parallel on-chip gene synthesis and application to optimization of protein expression. Nat Biotechnol. 29, 449-52.

Reeder, J., et al., 2007. pknotsRG: RNA pseudoknot folding including near-optimal structures and sliding windows. Nucleic Acids Res. 35, W320-4.

Rivas, E., Eddy, S. R., 1999. A dynamic programming algorithm for RNA structure prediction including pseudoknots. J Mol Biol. 285, 2053-68.

Rocha, E. P., et al., 1999. Translation in Bacillus subtilis: roles and trends of initiation and termination, insights from a genome analysis. Nucleic Acids Res. 27, 3567-76.

Sharp, P. M., Li, W. H., 1987. The codon Adaptation Index—a measure of directional synonymous codon usage bias, and its potential applications. Nucleic Acids Res. 15, 1281-95.

Scholle, M. D., et al., 2004. In vivo biotinylated proteins as targets for phage-display selection experiments. Protein Expr Purif. 37, 243-52.

Schroeder, S. J., et al., 2011. Ensemble of secondary structures for encapsidated satellite tobacco mosaic virus RNA consistent with chemical probing and crystallography constraints. Biophys J. 101, 167-75.

Voss, B., et al., 2006. Complete probabilistic analysis of RNA shapes. BMC Biol. 4, 5.

Xayaphoummine, A., et al., 2005. Kinefold web server for RNA/DNA folding path and structure prediction including pseudoknots and knots. Nucleic Acids Res. 33, W605-10.

Xayaphoummine, A., et al., 2003. Prediction and statistics of pseudoknots in RNA structures using exactly clustered stochastic simulations. Proc Natl Acad Sci USA. 100, 15310-5.

Zuker, M., Stiegler, P., 1981. Optimal computer folding of large RNA sequences using thermodynamics and auxiliary information. Nucleic Acids Res. 9, 133-48.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A method of preparing an expression vector, wherein the expression vector comprises, in order of position: a first nucleic acid sequence encoding a 5' untranslated region of an expressed mRNA that comprises a ribosome binding site (RBS); a second nucleic acid sequence encoding at least one polypeptide tag; and a cloning site, wherein the cloning site enables a target protein coding sequence to be inserted into the vector in-frame with the second nucleic acid sequence to encode a fusion protein comprising the at least one polypeptide tag and the target protein; and wherein the method comprises 1) specifically modifying the nucleic acid sequence encoding (i) the 5' untranslated region and (ii) the at least one adjacent polypeptide tag to minimize RNA secondary structure both within and/or between these two regions of the mRNA; and 2) introducing at least one silent mutation into the second nucleic acid sequence, wherein the at least one silent mutation increases the Codon Adaptation Index (CAI) value of the second nucleic acid sequence.

2. The method of claim 1, wherein nucleotides within about the last 100 nucleotides of the first nucleic acid sequence are modified.

3. The method of claim 1, wherein nucleotides within about the first 90 nucleotides of the second nucleic acid sequence are modified.

4. The method of claim 1, wherein the expression vector further comprises a target protein coding sequence inserted into the vector in-frame with the second nucleic acid sequence encoding at least one polypeptide tag, to encode a fusion protein comprising the at least one polypeptide tag and the target protein.

5. The method of claim 4, wherein the target protein coding sequence is not modified to minimize RNA secondary structure and/or is not modified to increase the Codon Adaptation Index (CAI) value of the target protein coding sequence.

6. The method of claim 4, wherein the target protein coding sequence encodes a transcription factor, a transcription factor domain, an epigenetic regulatory factor, or an epigenetic regulatory factor domain.

7. The method of claim 4, wherein the target protein coding sequence encodes a protein antigen for producing an affinity capture reagent.

8. The method of claim 4, wherein the expression of the target protein is 1.5 fold greater than the expression of a target protein generated from an expression vector that was not modified as described in claim 1.

9. The method of claim 1, wherein the second nucleic acid sequence encodes at least one affinity purification tag and/or at least one solubility enhancement tag.

10. The method of claim 1, wherein the second nucleic acid sequence is at least 60 nucleotides in length.

11. The method of claim 1, wherein the second nucleic acid sequence is at least 90 nucleotides in length.

12. An expression vector prepared using the method of claim 1.

13. An expression vector comprising, in order of position: a first nucleic acid sequence encoding a 5' untranslated region of an expressed mRNA that comprises a ribosome binding site (RBS); a second nucleic acid sequence encoding at least one polypeptide tag; and a cloning site, wherein the cloning site enables a target protein coding sequence to be inserted into the vector in-frame with the second nucleic acid sequence to encode a fusion protein comprising the at least one polypeptide tag and the target protein; wherein the nucleic acid sequence encoding (i) the 5' untranslated region and (ii) the at least one adjacent polypeptide tag has been specifically modified to minimize RNA secondary structure both within and/or between these two regions of the mRNA; and wherein the second nucleic acid sequence has been specifically modified to introduce at least one silent mutation, wherein the at least one silent mutation increased the Codon Adaptation Index (CAI) value of the second nucleic acid sequence.

14. The expression vector of claim 13, further comprising a target protein coding sequence inserted into the vector in-frame with the second nucleic acid sequence encoding at least one polypeptide tag, to encode a fusion protein comprising the at least one polypeptide tag and the target protein.

15. The expression vector of claim 14, wherein the target protein coding sequence has not been modified to minimize RNA secondary structure and/or has not been modified to increase the Codon Adaptation Index (CAI) value of the target protein coding sequence.

16. The expression vector of claim 14, wherein the target protein coding sequence encodes a transcription factor, a transcription factor domain, an epigenetic regulatory factor, or an epigenetic regulatory factor domain.

17. The expression vector of claim 14, wherein the target protein is expressed at a 1.5-fold higher level than a target protein generated from an expression vector that was not modified as described in claim 13.

18. The expression vector of claim 13, wherein the second nucleic acid sequence encodes at least one affinity purification tag and/or at least one solubility enhancement tag.

19. The expression vector of claim 13, wherein the second nucleic acid sequence is at least 60 nucleotides in length.

20. The expression vector of claim 13, wherein the second nucleic acid sequence is at least 90 nucleotides in length.

21. A host cell comprising the expression vector of claim 14.

22. A method for expressing a target protein in a host cell, comprising culturing the host cell of claim 21 for a period of time under conditions permitting expression of the target protein.

* * * * *

UNITED STATES PATENT AND TRADEMARK OFFICE
CERTIFICATE OF CORRECTION

PATENT NO. : 10,385,350 B2
APPLICATION NO. : 14/883277
DATED : August 20, 2019
INVENTOR(S) : Thomas B. Acton et al.

Page 1 of 1

It is certified that error appears in the above-identified patent and that said Letters Patent is hereby corrected as shown below:

In the Specification

Column 1, Lines 19-25, please delete "This invention was made with government support under U54-GM074958 awarded by the National Institute of General Medical Sciences Protein Structure Initiative and U01-DC011485 awarded by the National Institute on Deafness and other Communication Disorders under the auspices of the NIH Common Fund. The government has certain rights in the invention." and insert -- This invention was made with government support under grant number GM074958 awarded by the National Institutes of Health. The government has certain rights in the invention. -- therefor.

Signed and Sealed this
Twenty-seventh Day of December, 2022

Katherine Kelly Vidal
*Director of the United States Patent and Trademark Office*